US006573438B1

(12) United States Patent
Mettler et al.

(10) Patent No.: US 6,573,438 B1
(45) Date of Patent: *Jun. 3, 2003

(54) INBRED MAIZE LINE 2044BT

(75) Inventors: Irvin J. Mettler, Richmond, CA (US); David Mies, St. Joseph, IL (US)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/289,170

(22) Filed: Apr. 9, 1999

Related U.S. Application Data

(63) Continuation of application No. 09/042,426, filed on Mar. 13, 1998, now Pat. No. 6,114,608, and a continuation of application No. 08/818,573, filed on Mar. 14, 1997, now abandoned.

(51) Int. Cl.⁷ .............................. A01H 5/00; A01H 5/10; A01H 1/00
(52) U.S. Cl. .................... 800/320.1; 800/265; 800/275; 800/302
(58) Field of Search .............................. 800/320.1, 260, 800/275, 278, 279, 298, 302, 265

(56) References Cited

U.S. PATENT DOCUMENTS

| | | | |
|---|---|---|---|
| 4,945,050 A | | 7/1990 | Sanford, et al. |
| 5,304,714 A | * | 4/1994 | Miller ........................ 800/200 |
| 5,350,689 A | | 9/1994 | Shillito et al. |
| 5,371,003 A | | 12/1994 | Murry et al. |
| 5,484,956 A | | 1/1996 | Lundquist et al. |
| 5,500,365 A | | 3/1996 | Fischhuff et al. |
| 5,508,468 A | * | 4/1996 | Lundquist et al. .......... 800/205 |
| 5,561,236 A | | 10/1996 | Leemans et al. |

FOREIGN PATENT DOCUMENTS

| | | |
|---|---|---|
| EP | 0 292 435 | 11/1988 |
| EP | 0 465 875 | 1/1992 |
| EP | 0 469 273 | 2/1992 |
| EP | 0 604 662 A1 | 7/1994 |

OTHER PUBLICATIONS

UPOVROM, 222 US0000019869, Zea Mays, 2044Bt.*
Bedford et al, Gene 104: 39–45 (1991).
Bevan, M., et al., 1983. Nucleic Acids Res. 11:369–385.
Crickmore et al., Abstracts 28th Ann. Meeting Soc. Invert. Path. (1995), P14, Soc. Invert. Path., Bethesda MD.
Crossway et al., BioTechniques 4: 320–334 (1986).
Dennis, E.S., et al., 1984. Nucleic Acid Res. 12:3983–4000.
Franck, A., et al., 1980. Cell 21:285–294.
Gordon–Kamm et al., Plant Cell 2:603–618 (1990).
Gardner, R.C., et al., 1981. Nucleic Acids Res. 9:2871–2888.
Hinchee et al., BioTechnology 6: 915–922 (1988).
Hofte and Whiteley, Microbiol. Rev., 1989, 53:242–255.
Klein et al., Proc. Natl. Acad. Sci. USA, 85:4305–4309 (1988).
Klein et al., Bio/Technology 6:559–563 (1988).
Weising et al., Annual Rev. Genet. 22:421–477 (1988).
Norrander, J. M., et al., 1983. Gene 26:101–106.
Paszkoski et al., EMBO J. 3:2717–2722 (1984).
Potrykus, I. Annu. Rev. Plant Physiol. Plant Mol. Biol. 1991, 42: 205–225.
Riggs et al., Proc. Natl, Acad. Sci. USA 83:5602–5606 (1986).
Thompson C.J. et al., EMBO J., vol. 6:2519–2523 (1987).
Vasil et al., Bio/Technology 11:1553–1558 (1993).
Wohlleben et al. Gene 70:25–37 (1988).
Yamamoto and Powell, Advanced Engineered Pesticides, edited by Leo Kim, Marcel Dekker, Inc. 1993, 3–42.

* cited by examiner

*Primary Examiner*—Gary Benzion
*Assistant Examiner*—Melissa L. Kimball
(74) *Attorney, Agent, or Firm*—Bruce Vrana

(57) ABSTRACT

The present invention is drawn to a novel DNA construct comprising an expression cassette having a constitutive promoter which functions in plant cells operably linked to a maize alcohol dehydrogenase intron, a DNA sequence of a gene encoding a Cry 1Ab protein, and a terminator functional in plants and optionally further comprising a second cassette including a promoter which functions in plants operably linked to a maize alcohol dehydrogenase intron, a DNA sequence of a gene encoding for phosphinothricin acetyl transferase, and a terminator functional in plants wherein the two cassettes are transcribed in the same direction. Also provided are transgenic plants, particularly maize plants, having such a construct stably incorporated into their genomes.

12 Claims, 4 Drawing Sheets

INBRED MAIZE LINE 2044BT

This application is a continuation of U.S. application Ser. No. 09/042,426, filed Mar. 13, 1998, now U.S. Pat. No. 6,114,608 contents of which are incorporated herein by reference, which of U.S. application Ser. No. 08/818,573, filed Mar. 14, 1997 abandoned, initially filed as a regular U.S. application and subsequently converted to a provisional U.S. application, the contents of which are incorporated herein by reference.

BACKGROUND OF THE INVENTION

This invention relates to a novel promoter, a novel DNA construct containing the promoter and a Bt gene, and plants, especially corn plants, containing the novel DNA construct.

*Bacillus thuringiensis* (Bt) belongs to a large group of gram-positive, aerobic, endospore forming bacteria. During sporulation, these specific bacteria produce a parasporal inclusion body which is composed of insecticidally active crystalline protoxins, also referred to as δ-endotoxins.

These endotoxins are responsible for the toxicity of *Bacillus thuringiensis* to insects. The endotoxins of the various *Bacillus thuringiensis* strains are characterized by high specificity with respect to target organisms. With the introduction of genetic engineering it has become possible to create recombinant Bt strains which may contain a chosen array of insect toxin genes, thereby enhancing the degree of insecticidal activity against a particular insect pest.

The insecticidal crystal proteins from Bt have been classified based upon their spectrum of activity and sequence similarity (Hofte and Whiteley, Microbiol. Rev., 1989, 53:242–255 and Yamamoto and Powell, Advanced Engineered Pesticides, 1993, 3–42). Hofte and Whiteley published a classification scheme for the cry genes. Type I genes were considered active only against Lepidoptera species; Type II genes were active against Lepidoptera and Diptera species; Type III genes were active against Coleoptera species and Type IV genes included both 70- and 130-kDa crystal protein and were highly active against mosquito and blackfly larvae. However, since this original classification many novel cry genes have been cloned and sequenced demonstrating that the original system based on insect specificity required modification. A classification based on sequence homology along with new nomenclature based solely on amino acid identity has been proposed. (See Crickmore et al., Abstracts 28th Ann. Meeting Soc. Invert. Path. (1995), p14, Soc. Invert. Path., Bethesda Md.).

In this invention, the Cry proteins which are particularly effective against Lepidoptera species are preferred. These proteins are encoded by the following nonlimiting group of genes: cry1Aa, cry1ab, cry1Ac, cry1B, cry1C, cry1D, cry1E, cry1F, cry1G, cry2A, cry9C, cry5 and fusion proteins thereof. Among the cry genes, cry1Aa, cry1Ab, and cry1Ac show more than 80% amino acid identity and cry1Ab appears to be one of the most widely distributed cry genes. The Cry1Ab proteins are particularly effective against larvae of Lepidoptera (moths and butterflies).

The ingestion of these proteins, and in some cases the spores, by the target insect is a prerequisite for insecticidal activity. The proteins are solubilized in the alkaline conditions of the insect gut and proteolytically cleaved to form core fragments which are toxic to the insect. The core fragment specifically damages the cells of the midgut lining, affecting the osmotic balance. The cells swell and lyse, leading to eventual death of the insect.

A specific Lepidoptera insect, *Ostrinia nubilalis* (European corn borer (ECB)), causes significant yearly decrease in corn yield in North America. One study reveales that approximately 10% of the corn acres planted in the State of Illinois experienced a 9 to 15 percent annual yield loss, attributable solely to damage caused by the second generation of corn borer. Other important lepidopteran insect pests of corn include *Diatraea grandiosella* (Southwestern Corn Borer), *Helicoverpa zea* (Corn Earworm) and *Spodoptera frugiperda* (Fall Armyworm). The management practices of planting resistant or tolerant corn hybrids and treatment with chemical and microbial insecticides have not been satisfactory due to the low level of control provided by insecticidal treatments and the lack of hybrid lines resistant to second generation corn borers. Further tolerant and resistant hybrids often do not yield as well when infestation of ECBs are heavy. The use of corn genetically engineered to be resistant to specific corn insect pests has many advantages and these include a potential for substantial reduction in chemical insecticides and selective activity of the engineered endotoxin which will not disrupt the population of beneficial non-target insect and animals.

Toxic Bt genes from several subspecies of Bt have been cloned and recombinant clones have been found to be toxic to lepidopteran, dipteran and coleopteran insect larvae. However, in general, the expression of full length lepidopteran specific Bt genes has been less than satisfactory in transgenic plants (Vaeck et al, 1987 and Barton et al, 1987). It has been reported that the truncated gene from Bt kurstaki may lead to a higher frequency of insecticidal control. (U.S. Pat. No. 5,500,365). Modification of the existing coding sequence by inclusion of plant preferred codons including removal of ATTTA sequences and polyadenylation signals has increase expression of the toxin proteins in plants. (U.S. Pat. No. 5,500,365). In the present invention a truncated Bt kurstaki HD-1 gene has been used.

The instant invention additionally includes a second coding segment. The second coding segment comprises a DNA sequence encoding a selective marker for example, antibiotic or herbicide resistance including cat (chloramphenicol acetyl transferase), npt II (neomycin phosphototransferase II), PAT (phosphinothricin acetyl transferase), ALS (acetolactate synthetase), EPSPS (5-enolpyruvyl-shikimate-3-phosphate synthase), and bxn (bromoxynil-specific nitrilase). A preferred marker sequence is a DNA sequence encoding a selective marker for herbicide resistance and most particularly a protein having enzymatic activity capable of inactivating or neutralizing herbicidal inhibitors of glutamine synthetase. The non-selective herbicide known as glufosinate (BASTA® or LIBERTY®) is an inhibitor of the enzyme glutamine synthetase. It has been found that naturally occurring genes or synthetic genes can encode the enzyme phosphinothricin acetyl transferase (PAT) responsible for the inactivation of the herbicide. Such genes have been isolated from Streptomyces. These genes including those that have been isolated or synthesized are also frequently referred to as bar genes. As used herein the terms "bar gene" and "pat gene" are used interchangeably. These genes have been cloned and modified for transformation and expression in plants (EPA 469 273 and U.S. Pat. No. 5,561,236). Through the incorporation of the pat gene, corn plants and their offspring can become resistant against phosphinothricin (glufosinate).

SUMMARY OF THE INVENTION

Figure 1:
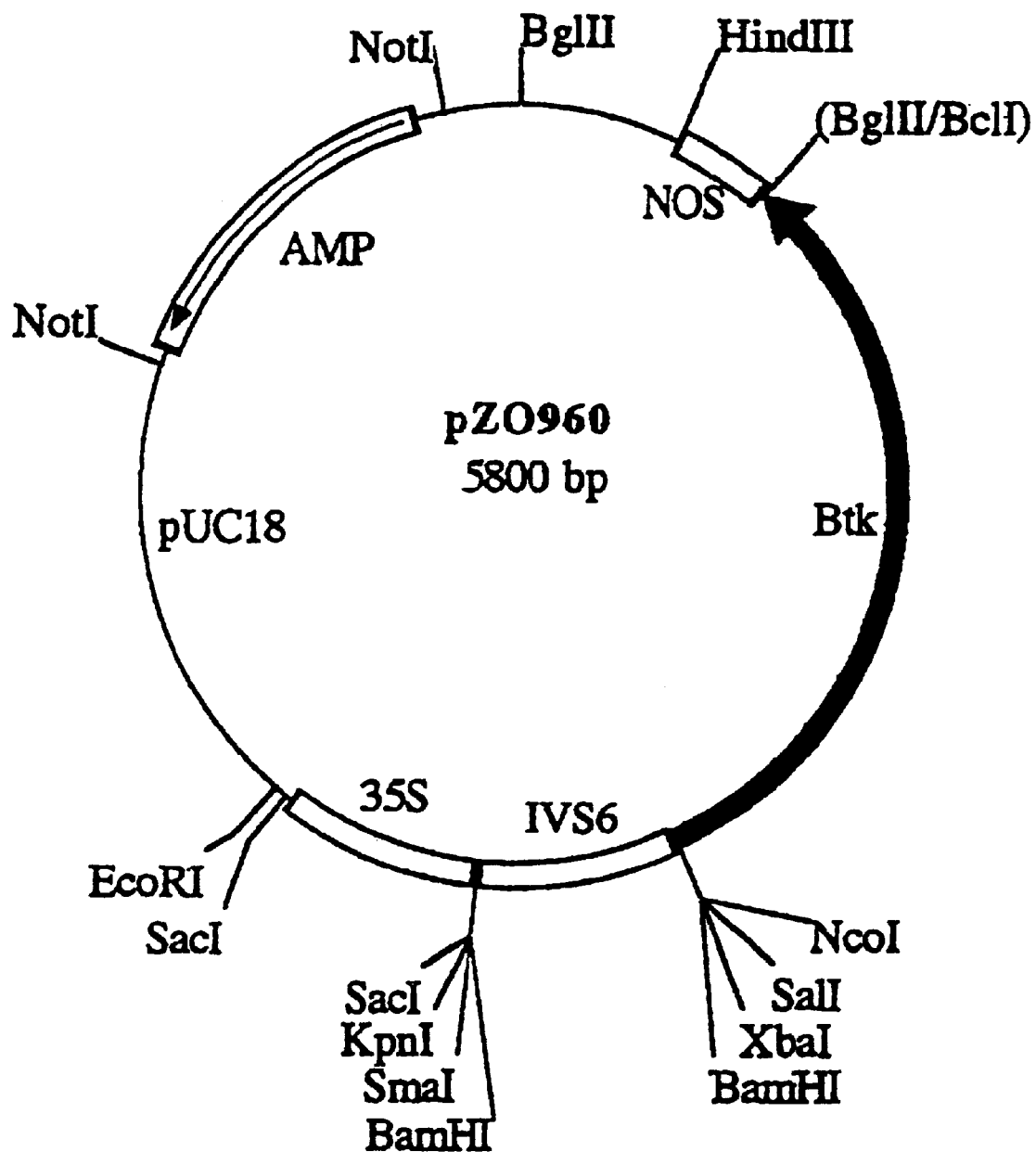
FIG. 1 represents a plasmid map of pZO960 which contains the Bt kurstaki expression cassette.

The present invention is drawn to a novel recombinant DNA construct comprising an expression cassette includes a constitutive promoter which functions in plant cells operably linked to an intron that functions in monocots; a DNA sequence of a gene encoding an insecticidal *Bacillus thuringiensis* protein toxin; and a terminator functional in plants; and optionally further comprises a second cassette which includes a promoter which functions in plant cells operably linked to an intron that functions in monocots; a DNA sequence of a gene encoding for phosphinothricin acetyl transferase; and a terminator functional in plants, wherein the two cassettes are transcribed in the same direction.

Therefore a first aspect of the present invention is a DNA construct which expresses the crystal protein toxin of a Bt effective against Lepidopteran insects at relatively high levels and further provides resistance to the non-selective herbicide glufosinate.

A second aspect of the invention is a plant transformation vector comprising the DNA construct as given above.

A third aspect of the present invention comprises a transformed plant cell including the DNA construct as given above wherein the DNA is stably incorporated in the plant genome.

A fourth aspect of the invention is a plant comprising transformed plant cells wherein the DNA construct as given above is stably incorporated into the genome of the plant.

The invention further encompasses plant seeds having the DNA construct as given above stably incorporated therein.

Another aspect of the invention includes a plant cell co-transformed with a first nucleic acid construct comprising, a CaMV 35S constitutive promoter which functions in plant cells operably linked to a maize alcohol dehydrogenase intron, a DNA sequence of a gene encoding a Cry1Ab protein toxin or a functionally related protein toxin, and a terminator functional in plants and a second nucleic acid construct comprising a CaMV 35S promoter which functions in plant cells operably linked to a maize alcohol dehydrogenase intron, a DNA sequence of a gene encoding for phosphinothricin acetyl transferase, and a terminator functional in plants wherein the first and second constructs are stably integrated in the plant genome.

The DNA construct of the invention preferably is an expression cassette functional in a plant comprising a promoter functional in plants, for example a CaMV 35S promoter, e.g., as disclosed in SEQ ID No. 1 or 5, preferably SEQ ID No. 1, operably linked to an intron which functions in monocots, for example a maize alcohol dehydrogenase intron, e.g., as disclosed in SEQ ID No. 2 or 6, preferably SEQ ID No. 2. This promoter/intron sequence is operably linked to a DNA sequence of interest, for example a gene encoding a Bt delta-δ-endotoxin, e.g., encoding the toxin domain of a Cry1Ab protein or a functionally related toxin protein, preferably modified for expression in plants, for example as depicted in SEQ ID No. 3, or a gene for a selectable marker, for example a gene for herbicide resistance, preferably glufosinate resistance, for example a Pat gene, e.g., as depicted in SEQ ID No. 7. The gene of interest is suitably linked to a terminator functional in plants, e.g. a Nos terminator, for example as disclosed in SEQ ID No. 4 or 8, preferably SEQ ID No. 4, to form an expression cassette functional in a plant. Especially preferred embodiments of the Bt expression cassette comprise SEQ ID Nos. 1, 2, 3 and 4 in operable sequence, e.g., as in the Btk cassette described below. Especially preferred embodiments of a Pat expression cassette comprise SEQ ID Nos. 5, 6, 7, and 8 in operable sequence. In an especially preferred embodiment, a Bt expression cassette as described herein is linked on the same DNA with a Pat expression cassette as described herein, e.g., a plasmid comprising cassettes formed by SEQ ID Nos. 1–4 and 5–8 wherein the two cassettes are transcribed in the same direction, e.g., as in plasmid pZO1502.

The use of such expression cassettes in a method of transforming plants, e.g., maize plants, for example a method or biolistic or protoplast transformation of maize plants, especially protoplast transformation as described in the examples herein is also provided, as are plants stably transformed with expression cassettes as described, particularly maize plants, e.g., field corn, sweet corn, white corn, silage corn and popcorn, and seed thereof. Particularly preferred are maize plants and seed thereof descended from the Bt11 transformation event described in Example 2, for example Maize containing the Btk construct described within a 15 cM region of chromosome 8, near position 117, in the approximate position of public probe UMC30a, in the interval flanked by two markers: Z1B3 and UMC150a, preferably (i) elite inbred sweet corn lines R327H, R372H, R412H, R583H and R660H, (ii) elite inbred field corn lines 2043Bt, 2044Bt, 2070Bt, 2100Bt, 2114Bt, 2123Bt, 2227Bt, 2184Bt, 2124Bt, and 2221Bt, and (iii) maize inbred varieties descended from the same transgenic event as these lines which contain and express the same transgenic construct, including seed thereof.

When particular inbred varieties are identified herein, it is understood that the named varieties include varieties which have the same genotypic and phenotypic characteristics as the identified varieties, i.e., are derived from a common inbred source, even if differently named. The invention also provides hybrid maize seed produced by crossing plants of an inbred corn line as described above with plants of having a different genotype, and hybrid corn plants produced by growing such hybrid maize seed. Also provided is a method of producing hybrid maize seeds comprising the following steps:

A. planting in pollinating proximity seeds of a first inbred maize line as described herein and seeds of a second inbred line having a different genotype;

B. cultivating maize plants resulting from said planting until time of flowering;

C. emasculating said flowers of plants of one of the maize inbred lines;

D. allowing pollination of the other inbred line to occur, and

E. harvesting the hybrid seeds produced thereby.

Also provided are hybrid seeds produced by this method, F1 hybrid plants produced by growing such seeds, and parts of such F1 hybrid plants, including seeds thereof.

Seeds of the plants described herein (e.g., of maize plants, e.g., Bt11 maize plants, for example inbred or hybrid seeds as described above) for planting purposes is preferably containerized, e.g., placed in a bag or other container for ease of handling and transport and is preferably coated, e.g., with protective agents, e.g., safening or pesticidal agents, in particular antifungal agents and/or insecticidal agents. One particular embodiment of this invention is isolated inbred seed of the plants described herein, e.g. substantially free from hybrid seed or seed of other inbred seed, e.g., a seed lot or unit of inbred seed which is at least 95% homogeneous, e.g., isolated seed of any of the maize inbreds described in example 8 or 9 hereof.

Also provided herein, for the first time, are Bt maize varieties other than Bt field corn, particularly Bt sweet corn. Although Bt field corn has been disclosed, it was not previously determined experimentally whether or how a Bt delta δ-endotoxin would interact with traits associated with sweet corn, which is harvested at an earlier maturity (before it is dry), for a different purpose (usually fresh produce, canning or freezing, for human consumption) and has been bred therefore to be qualitatively and quantitatively different from field corn in a number of respects. Therefore, in one embodiment, the invention comprises a sweet corn comprising in its genome an expression cassette comprising a coding region for a Bt delta-δ-endotoxin or functional fragment or derivative thereof, under control of a promoter operable in maize, e.g., an expression cassette as described herein. The sweet corn of the invention includes sweet or supersweet maize having a higher sugar to starch ratio than field corn (e.g., yellow dent corn) due to a reduced capacity to convert sugar into starch, typically characterized by a sugary (su, e.g., su1) allele in the case of sweet corn, and/or shrunken allele (sh, e.g., sh2) or brittle allele (bt, e.g., bt2, not to be confused with the gene for an endoxin from *Bacillus thuringiensis*, described elsewhere herein) in the case of supersweet corn, especially maize containing the su1 or sh2 alleles.

Bt maize of the invention, e.g., Bt11 maize, is found to be particularly suited for the preparation of food materials (e.g., for human or animal consumption, for example sweet corn for for packaging or fresh use as a human food, or grain or silage made from field corn) containing reduced levels of fungal toxins, e.g., aflatoxins. While the mechanism is not entirely understood, in grain and silage made from Bt11 maize, the level of aflatoxin is believed to be lower, possibly because the reduction in insect damage reduces the level of opportunistic fungal infection in the growing plant. Accordingly, food materials made from Bt maize of the invention, particularly Bt11 maize, for example grain and silage having reduced levels of fungal toxins, particualrly aflatoxins, and the use of the Bt maize of the invention in a method of preparing a foodstuff, especially grain or silage, with reduced levels of fungal toxins, e.g., aflatoxins, is also provided.

DETAILED DESCRIPTION OF THE INVENTION

A promoter is defined as a nucleotide sequence at the 5' end of a structural gene which directs the initiation of transcription. The structural gene is placed under regulatory control of the promoter. Various promoters which are active in plant cells are known and described in the art. These include Cauliflower Mosaic Virus (CaMV) 19S and 35S; nopaline synthase (NOS); mannopine synthase (MAS); actin; ubiquitin; ZRP; chlorophyll AB binding protein (CAB); ribulose bisphosphate carboxylase (RUBISCO); heat shock Brassica promoter (HSP 80); and octopine synthase (OSC). The particular promoter used in the present invention should be capable of causing sufficient expression to result in production of an effective amount of protein. The promoter used in the invention may be modified to affect control characteristics and further may be a composite of segments derived from more than one source, naturally occurring or synthetic. The preferred promoters are CaMV promoters and particularly CaMV 35S. The term "CaMV 35S" includes variations of the promoter wherein the promoter may be truncated or altered to include enhancer sequences, to increase gene expression level, and composite or chimeric promoters, wherein portions of another promoter may be ligated onto the CaMV 35S. A preferred embodiment includes the 5' untranslated region of the native 35S transcript, and more particularly wherein the untranslated region includes about 100 to 150 nucleotides. Additionally while 35S promoters are fairly homologous, any 35 S promoter in a preferred embodiment would include the untranslated region of the native 35S transcript. Particularly preferred 35S promoters are described in SEQ ID NO. 1 and SEQ ID NO. 5. The promoter as described in SEQ ID NO. 1 as part of the claimed construct may have particular advantage in that the construct may be expressed in pollen tissue.

An intron is a transcribed nucleotide sequence that is removed from the RNA transcript in the nucleus and is not found in the mature mRNA. Such sequences are well known in the art, and monocot introns include but are not limited to sucrose synthetase (SS); glutathione transferase; actin; and maize alcohol dehydrogenase introns. An exon is part of a gene that is transcribed into a mRNA and includes non-coding leader and/or trailer sequences. An exon may code for a specific domain of a protein. Having native exon sequences around an intron may improve the introns splicing activity or the ability of the nuclear splicesomal system to properly recognize and remove the intron. According to the invention, a preferred embodiment includes the native exon in the first cassette and more particularly 50 or more nucleotide bases of the native exon on each side of the intron is preferred.

A gene refers to the entire DNA sequence involved in the synthesis of a protein. The gene includes not only the structural or coding portion of the sequence but also contains a promoter region, the 3' end and poly(A) sequences, introns and associated enhancers or regulatory sequences.

A structural heterologous gene is that part of a DNA segment which encodes a protein, polypeptide or a portion thereof, and one which is not, normally found in the cell or in the cellular location where it is introduced. The DNA sequence of a structural heterologous gene of the present invention include any DNA sequence encoding a crystal toxin insecticidal protein. The preferred toxins include but are not limited to Cry1Aa, Cry1Ab, Cry1Ac, Cry1B, Cry1C, Cry1D, Cry1E, Cry1F, Cry1G, Cry2A, Cry2B, Cry3A, Cry3B, Cry3C, Cry4A, Cry4B, Cry4C, Cry4D, Cry5A, Cry9C, CytA and any fusion protein or truncated gene that encodes one or more of the abovementioned toxins or a mixture thereof. Particularly preferred toxins include Cry1Aa, Cry1Ab, Cry1Ac, Cry1C, Cry2A, Cry3C, Cry1E, Cry5A, Cry9C and any mixture or fusion protein thereof. In the present specification, the term fusion protein is used interchangeably with the terms fusion toxin and hybrid protein and is a protein consisting of all or part of an amino acid sequence (known as a domain) of two or more proteins, and is formed by fusing the protein encoding genes. An example of a DNA sequence useful in the cassette of this invention is a DNA sequence encoding a fusion toxin wherein the toxin is Cry1Ab/Cry1C and Cry1E/Cry1C. The domains comprising the fusion protein may be derived from either naturally occurring or synthetic sources.

Many cry1Ab genes have been cloned and their nucleotide sequences determined. A holotype gene sequence of cry1Ab has accession number M13898 (The GenBank v. 70/EMBL v.29). A number of studies reveal that the amino terminal end of the Cry1A protein is responsible for the insecticidal activity. This region depends on the particular protein but in general include a truncated gene that encodes from about amino acid 25 to amino acid 610 of the protein.

In the present invention, a preferred cry1Ab gene includes a synthetic gene encoding the toxin domain of the protein produced by the Bt kurstaki (k) HD-1 gene wherein the G+C content of the Btk gene is increased and the polyadenylation sites and ATTTA regions are decreased. U.S. Pat. No. 5,500,365, which is hereby incorporated in its entirety discloses a synthetic Btk HD-1 and HD-73 gene, and truncated HD-1 and HD-73 genes. A particularly preferred cry1Ab gene of this invention is the sequence as described in SEQ ID NO. 3.

Other preferred genes include those that are functionally equivalent to cry1Ab. These genes include all cry1Ab, cry1Aa, cry1Ac and variants thereof wherein the expressed protein toxin is active against one or more major maize Lepidoptera insect pests. The insect pests include the aforementioned European corn borer, Southwestern corn borer, Fall armyworm, and Corn earworm. The second structural gene that is part of the invention includes a DNA sequence encoding a selective marker for example, antibiotic or herbicide resistance including cat (chloramphenicol acetyl transferase), npt II (neomycin phosphototransferase II), PAT (phosphinothricin acetyltransferase), ALS (acetolactate synthetase), EPSPS (5-enolpyruvyl-shikimate-3-phosphate synthase), and bxn (bromoxynil-specific nitrilase). A preferred marker sequence is a DNA sequence encoding a selective marker for herbicide resistance and most particuarly a protein having enzymatic activity capable of inactivating or neutralizing herbicidal inhibitors of glutamine synthetase. The non-selective herbicide known as glufosinate (BASTA® or LIBERTY ®) is an inhibitor of the enzyme glutamine synthetase. It has been found that naturally occurring genes or synthetic genes can encode the enzyme phosphinothricin acetyl transferase (PAT) responsible for the inactivation of the herbicide. Such genes have been isolated from Streptomyces. Specific species include *Streptomyces hygroscopicus* (Thompson C. J. et al., EMBO J., vol. 6:2519–2523 (1987)), *Streptomyces coelicolor* (Bedford et al, Gene 104: 39–45 (1991)) and *Streptomyces viridochromogenes* (Wohlleben et al. Gene 80:25–57 (1988)). These genes including those that have been isolated or synthesized are also frequently referred to as bar genes. As used herein the terms "bar gene" and "pat gene" are used interchangeably. These genes have been cloned and modified for transformation and expression in plants (EPA 469 273 and U.S. Pat. No. 5,561,236). Through the incorporation of the pat gene, corn plants and their offspring can become resistant against phosphinothricin (glufosinate). A preferred coding segment of a bar gene of the present invention is the sequence described in SEQ ID NO. 7.

The structural gene of this invention may include one or more modifications in either the coding region or in the untranslated region which would not substantially effect the biological activity or the chemical structure of the expression product, the rate of expression or the manner of expression. These modifications include but are not limited to insertions, deletions, and substitutions of one or more nucleotides, and mutations. The term homology as used herein refers to identity or near identity of nucleotide or amino acid sequences. The extent of homology is often measured in terms of percentage of identity between the sequences being compared. It is understood in the art that modification can occur in genes and that nucleotide mismatches and minor nucleotide modifications can be tolerated and considered insignificant if the changes do not alter functionality of the final product. As in well known in the art the various cry1A genes have very similar identity and reference in made to the article by Yamamoto and Powell, Advanced Engineered Pesticides, 1993, 3–42 which includes a dendrogram table showing sequence homology among full length crystal proteins obtained from the GenBank data base for a full length comparision.

Termination sequences are sequences at the end of a transcription unit that signals termination of transcription. Terminators are 3' non-translated DNA sequences that contain a polyadenylated signal. Examples of terminators are known and described in the literature. These include but are not limited to nopline synthase terminator (NOS); the 35S terminator of CaMV and the zein terminator.

Other elements may be introduced into the construct for examples matrix attachments region elements (MAR). These elements can be positioned around an expressible gene of interest to effect an increase in overall expression of the gene and to diminish position dependent effects upon incorporation into the plant genome.

Transformation means the stable integration of a DNA segment carrying the structural heterologous gene into the genome of a plant that did not previously contain that gene. Co-transformation is transformation with two or more DNA molecules. Frequently one segment contains a selectable gene generally one for antibiotic or herbicide resistance.

As used herein the term plant tissue is used in a wide sense and refers to differentiated and undifferentiated plant tissue including but not limited to, protoplasts, shoots, leaves, roots, pollen, seeds, callus tissue, embryos, and plant cells (including those growing or solidified medium or in suspension.

The DNA construct of this invention may be introduced into a plant tissue by any number of art recognized ways. These included, but are not limited to, direct transfer of DNA into whole cells, tissue or protoplasts, optionally assisted by chemical or physical agents to increase cell permeability to DNA, e.g. treatment with polyethylene glycol, dextran sulfate, electroporation and ballistic implantation of DNA coated particles. The following references further detail the methods available: Biolistic transformation or microprojectile bombardment (U.S. Pat. No. 4,945,050; U.S. Pat. No. 5,484,956; McCabe et al., Annual Rev. Genet. 22:421–477 (1988); Klein et al., Proc. Natl. Acad. Sci. USA, 85:4305–4309 (1988); Klein et al., Bio/Technology 6:559–563 (1988); Gordon-Kamm et al., Plant Cell 2:603–618 (1990); and Vasil et al., Bio/Technogy 11:1553–1558 (1993); Protoplast transformation—EPA 0 292 435; EPA 0 465 875; and U.S. Pat. No. 5,350,689; microinjection—Crossway et al., BioTechniques 4:320–334 (1986); direct gene transfer—Paszkoski et al., EMBO J. 3:2717–2722 (1984); electrotransformation—U.S. Pat. No. 5,371,003; and electroporation—Rigg et al., Proc. Natl, Acad. Sci. USA 83: 5602–5606 (1986). Transformation is also mediated by Agrobacterium strains, notably *A. tumefaciens* and *A. rhizogenes,* and also by various genetically engineered transformation plasmids which include portions of the T-DNA of the tumor inducing plasmids of Agrobacteria. EPA 0 604 662A1, Japan Tobacco Inc.; Hinchee et al., BioTechnology 6: 915–921 (1988). Also see Potrykus, I. Annu. Rev. Plant Physiol. Plant Mol. Biol. 1991, 42:205–225. The choice of a particular method may depend on the type of plant targeted for transformation.

Transformed plants may be any plant and particularly corn, wheat, barley, sorghum, and rice plants, and more particularly corn plants derived from a transformant or backcrossing through further breeding experiments.

EXAMPLE 1: Plasmid construction

A. Plasmid pZO1502 construction: The plasmid pZO1502 can be considered to consist of three basic regions; the base plasmid vector, an expression cassette for the Btk gene, and an expression cassette for the pat gene. For convenience, the various parts were constructed separately and then combined into the final plasmid. In order to assemble the desired elements for the Btk and pat gene expression cassettes, the restriction sites used to generate the desired elements sometimes required modification. The following example demonstrates the procedure used to produce the pZO1502 plasmid. One skilled in the art could devise alternate ways to construct the final transformation plasmid.

Figure 2:
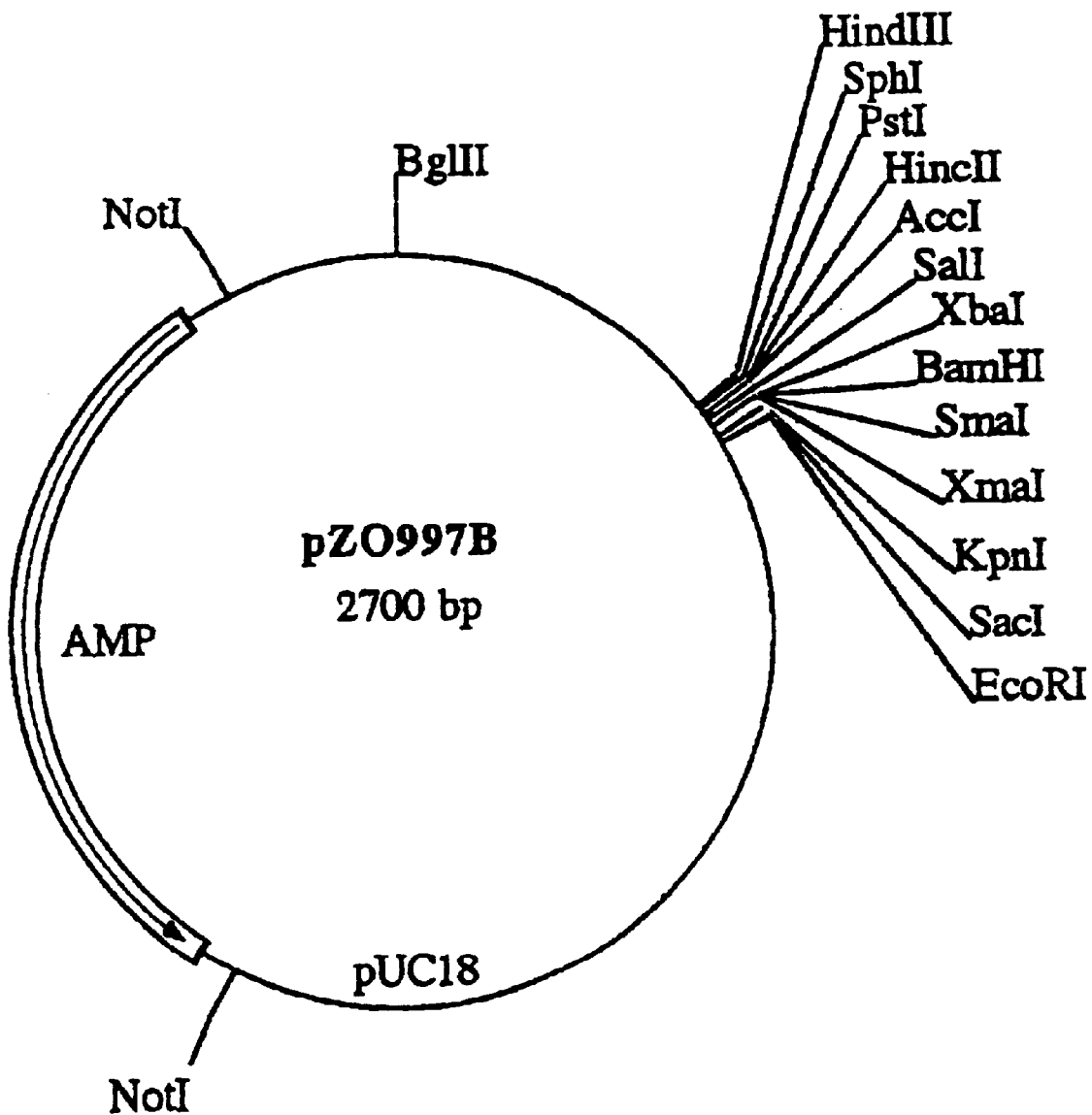
FIG. 2 represents a plasmid map of the base transformation vector pZO997

B. Base Plasmid Vector: The base vector, pUC18 (GenBank accession L08752, Norrander, J. M., et al., 1983. Gene 26:101–106), was modified by replacing the EcoO 109 I restriction site with a Bgl II linker (digestion with EcoO 109 I, fill in with T4 polymerase, and addition of a Bgl II linker). This base vector was further modified to replace the BspH I sites at 1526 and 2534 with Not I restriction sites (vector cut with BspH I, filled in, and replaced with Stu I linkers; the Stu I site was then cut and Not I linkers added). The addition of the Not I restriction sites provided a convenient way to produce a linear DNA fragment containing the two desired gene cassettes (Btk and pat) separated from the ampicillin gene sequence (required for plasmid production in *E. coli*). This linearization also significantly increased protoplast transformation frequency. The final base vector was named pZO997B (FIG. 2).

C. Btk gene expression cassette: The Dde I to Dde I fragment of the 35S promoter from cauliflower mosaic virus (strain CM1841, GenBank accession #V00140, Gardner, R. C., et al., 1981. *Nucleic Acids Res.* 9:2871–2888) (SEQ ID NO. 1) was converted to Sac I by addition of linkers and cloned into the Sac I site of the polylinker region of a pUC19 based vector. The sixth intron from maize Adh1-1S gene (GenBank accession X04049, Dennis, E. S., et al., 1984. *Nucleic Acid Res.* 12:3983–4000) was isolated as a Pst I to Hpa II fragment, converted with BamH I linkers (SEQ. ID NO. 2), and cloned into the BamH I poly linker site 3' to the 35S promoter. The 3' terminator from Nopaline synthetase, NOS, (GenBank accession V00087, Bevan, M., et al., 1983. *Nucleic Acids Res.* 11:369–385) (SEQ. ID NO 4) was isolated as ~250 bp fragment with Pst I and Bgl II. The Bgl II site was polished With T4 polymerase, a Hind III linker added, and the fragment inserted behind a gus gene construct using the Pst I and Hind III sites. The gus gene was cloned into the Sal I to Pst I site of the polylinker. The gus construct utilized a synthetic linker (Sal I to Nco I, which provides for an A nucleotide at the −3 position from the translation start ATG: GTCGACCATGG) (SEQ ID NO. 9). The Pst I site was then trimmed, a Bcl I linker added, and the gus gene sequence replaced with a synthetic gene encoding a cry1Ab toxin (SEQ. ID NO. 3) as a Nco I to Bgl II insert to produce the vector pZO960 (FIG. 1)

Figure 3:
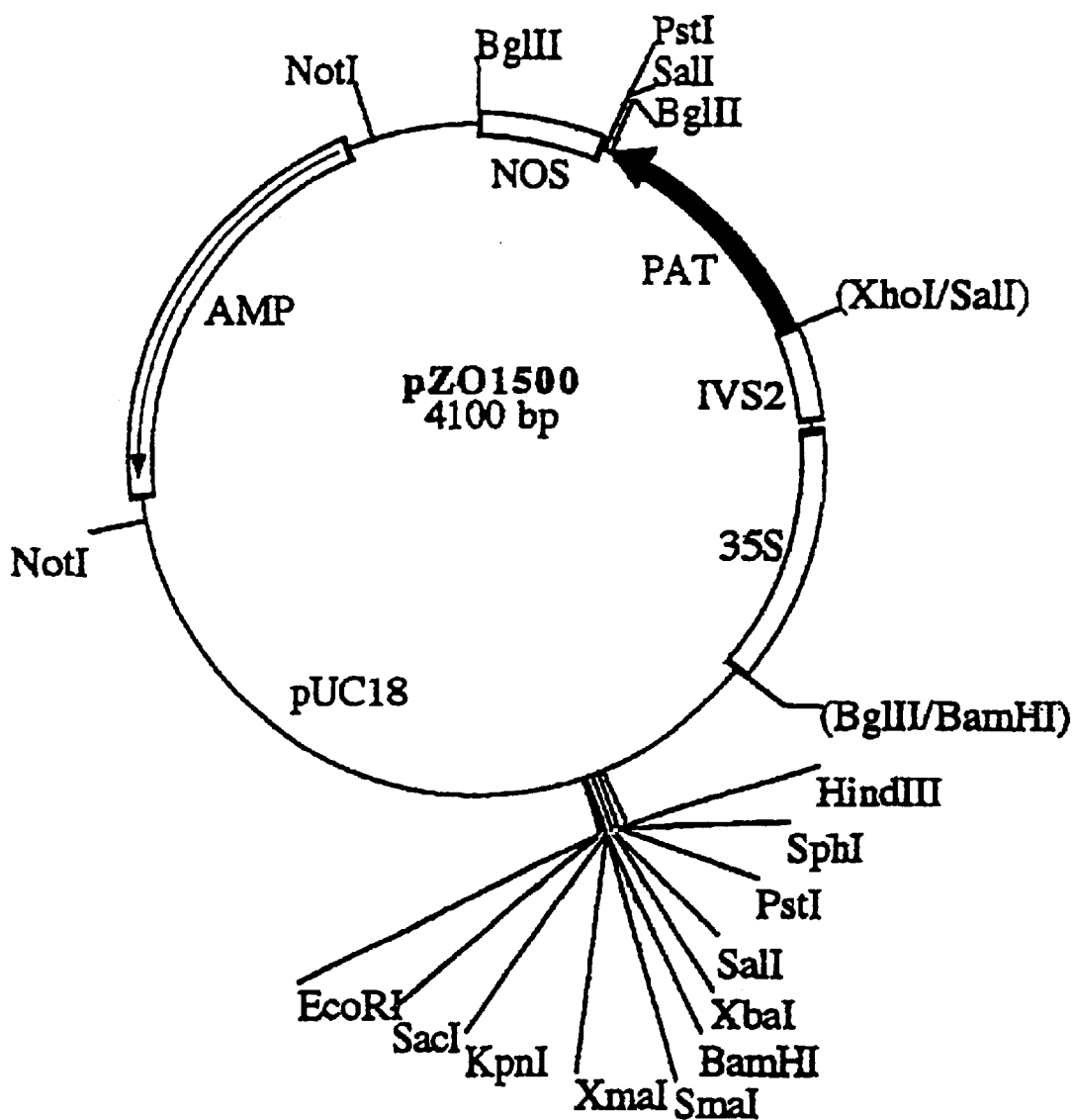
FIG. 3 represents a plasmid map of pZO1500 which contains the PAT cassette.

D. Pat gene expression cassette: Although composed of similar elements, the pat expression cassette was derived from a different series of cloning steps. The 35S promoter (SEQ ID NO. 5) was obtained as a Hinc II to Dde I fragment from the cauliflower mosaic virus (strain CABB-S, GenBank accession #V00141, Franck, A., et al., 1980. Cell 21: 285–294) and converted to BamH I—Xba I with linkers. The second intron sequence from maize Adh1-1S (GenBank accession X04049, Dennis, E. S., et al., 1984. *Nucleic Acid Res.* 12:3983–4000) (SEQ ID NO. 6) was isolated as a Xho II to Xho II fragment and cloned into the BamH I site of pUC12, converting the Xho II sites to BamH I. As a BamH I fragment it was cloned into the Bgl II site of a synthetic polylinker (Asu II, Bgl II, and Xho I). The Asu II site was then filled in and ligated to the (filled in) Xba I site of the 35S promoter fragment. The synthetic pat gene sequence was subcloned from plasmid pOAC/Ac (obtained from Dr. Peter Eckes, Massachusetts General Hospital, Boston Mass.) (SEQ ID NO. 7) as a Sal I to Pst I fragment and combined with the 35S/Adhivs2 promoter (Xho I) and the 3' NOS terminator sequence Pst I to Bgl II (GenBank accession V00087, Bevan, M., et al., 1983. *Nucleic Acids Res.* 11:369–385) (SEQ ID NO. 8). These pieces were all combined with the pZO997B base vector to produce the pat expression vector pZO1500 (FIG. 3).

Figure 4:
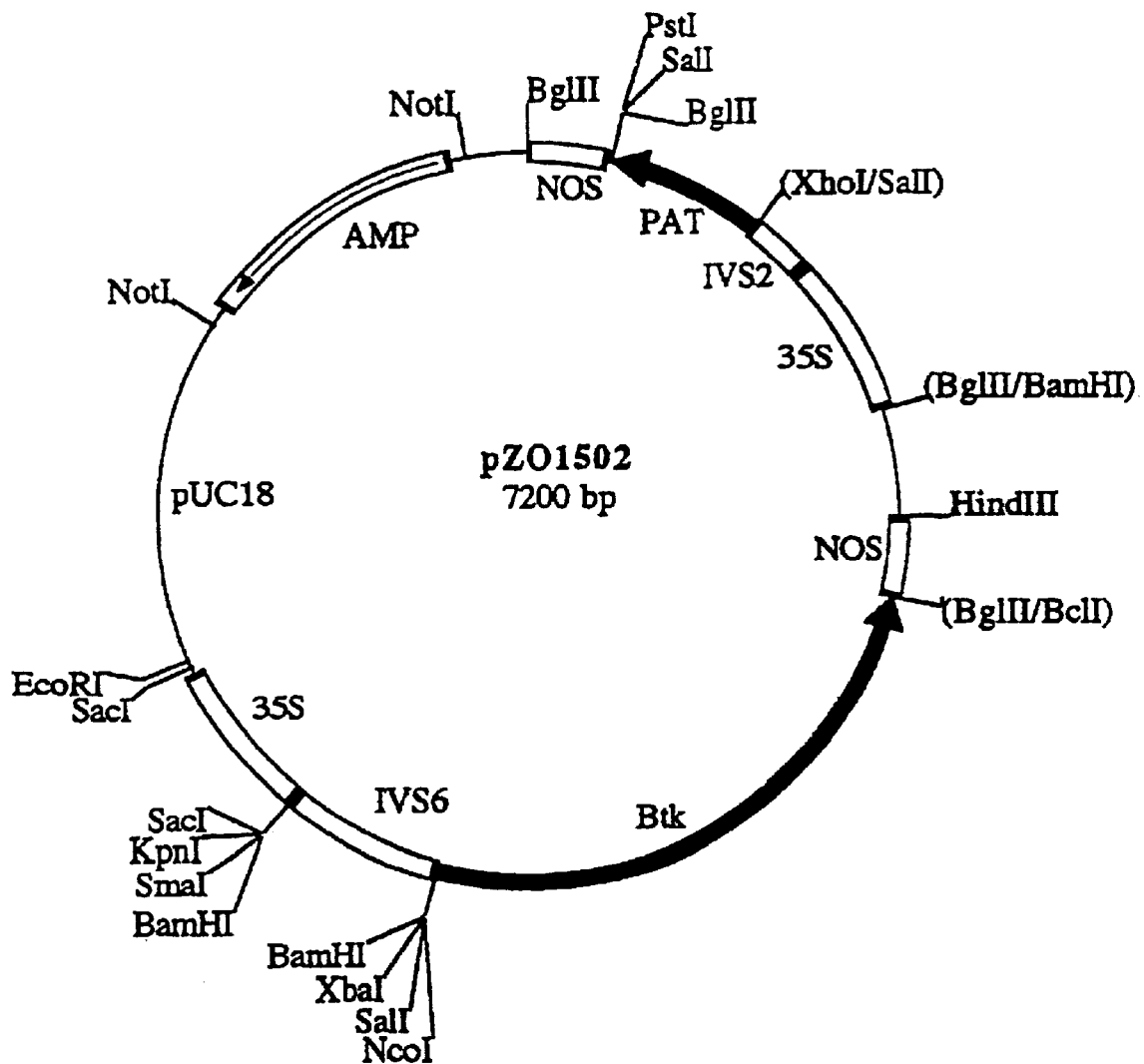
FIG. 4 represents a plasmid map of the (expression/transformation) vector pZO 1502 which contains the Bt kurstaki cassette and the PAT cassette.

As the final construction step, the Btk expression cassette was subcloned from pZO960 as an EcoR I-Hind III fragment and inserted into the EcoR I-Hind III polylinker site of pZO1500 to produce the final vector, pZO1502 (FIG. 4). The amp (beta-lactamase) gene was removed prior to plant transformation by digestion with NotI. pZO1502 has been deposited with the American Type Culture Collection (ATCC), 12301 Parklawn Drive, Rockville, Md. 20852–1776 USA pursuant to the Budapest Treaty prior to the filing of this application and accorded accession number 20982 on Mar. 13, 1998, and the complete sequence of this plasmid is disclosed in SEQ. ID No. 9.

EXAMPLE 2: Protoplast transformation, selection of transformed corn cells and regeneration The initial parental transformation of the corn line to be planted was accomplished through insertion of a DNA fragment from plasmid pZO1502, containing the two cassettes of Btk and the pat gene, into the genome of a proprietary corn cell line owned by Hoerchst AG (Frankfurt Germany). The transformation was performed using a protoplast transformation and regeneration system as described in detail in European Patent Application Publication Number 0 465 875 A, published Jan. 15, 1992 and European Patent Application Publication Number 0 469 273 A, published Feb. 5, 1992 and Theor. Appl. Gent. 80:721–726 (1990)). The contents of which are hereby incorporated by reference.

After some weeks on selective media putative transformant clumps of cells were observed and transformed protoplasts were selected in vitro with a glufosinate-ammonium herbicide. Sixteen leaf producing genetically transformed corn lines were obtained from protoplasts treated with the gene expression cassette from pZO1502. One of these lines was designated as transformant number 11. This transformant was grown to maturity.

The Bt-11 R0 transformed plants were pollinated with nontransformed Northrup King elite inbred male parents and $R_1$ seed was collected. Descendants of the initial crossing have been successively backcrossed and test crossed to establish and evaluate corn lines carrying the Btk gene. Such lines are described more fully in the Examples 8 and 9 below and have been deposited with the ATCC pursuant to the Budapest Treaty.

EXAMPLE 3: Stable Transformation

Expression of the Btk gene was tested by transforming the Bt gene vector pZO960 into BMS (Black Mexican Sweet)

corn cells. Protoplasts were isolated from a suspension culture BMS cell line and electroporated to induce DNA uptake essentially as described in Sinibaldi, R. M. and Mettler, I. J., 1992, In: Progress in Nucleic Acid Research and Molecular Biology (W. E. Cohn and K. Moldave, eds.) Academic Press, San Diego, vol. 42:229–259. Cells which had stably incorporated DNA were selected by co-transformation with a plasmid containing a kanamycin resistance selectable gene. A number of independent transgenic events were selected by the expression of the antibiotic resistance to kanamycin. Approximately 1 gram of each transgenic line was then used to test for biological activity against neonate larvae of Manducca sexta. Control, nontransformed, BMS callus tissue supported normal growth of the larvae throughtout the test period. Transgenic callus lines were then rated for the degree of growth inhibition. As shown in Table 1, out of 33 BMS lines co-transformed with pZO960, 6 lines were positive for insecticidal activity showing complete growth inhibition and 100% mortality within 2 or three days. Quantitative Elisa assays showed that the transgenic tissues produced an average of 3.1 ng of Bt protein per mg of total extracted protein.

TABLE 1

Stable Transformation with Btk Cassette

| Construct | Insect activity #pos/#test | Bt ELISA assays ng/mg protein |
|---|---|---|
| pZO960 | 6⁺/33 | 3.1 |

⁺= strong insecticidal activity, 100% mortality in 2–3 days, little feeding.

EXAMPLE 4: Insertion Site of Bt11 Transgenic Event

The original genetic stock into which the Btk sequence was transformed was designated HE89. The Ro plants were used as the female parent for initial crosses to two, elite Northrup King proprietary inbred lines for which Btk-conversion was sought. Multiple backcrosses were conducted into many additional inbred lines with individuals selected that contained the insertion sequence but were, otherwise, as similar to the elite recurrent parents as possible. Four or more backcrosses and selfing to homozygosity were used in the conversion process. Finished conversion stocks were evaluated with a series of 50 or 60 RFLP probes selected to be well distributed throughout the genome. Genotypes of the Btk converted inbreds were compared to those of their recurrent parent isolines. They were generally identical or nearly identical for all genetic markers, except for three probes on a small segment of the long arm of chromosome 8. All conversion stocks differ from the genotype of the transformed stock, HE89, for this segment, thus differing from the recurrent parents. There were no other genomic regions with consistent differences between Btk-conversions and their recurrent parents. These three probes exist within 10 centiMorgans(cM) of one another at the approximate position of the public probe UMC30a, which has been placed at map position 117 in the 1995 map of RFLP probe positions distributed by the University of Missouri at Columbia.

A series of 95 backcross progeny were further characterized with numerous probes in the region of chromosome 8 identified above. The size of the "donor" DNA segment varied among these progeny. However, five of the progeny failed to contain the donor alles at the flanking markers: Z1B3 and UMC150a, despite presence of the Btk sequence. These two probes are approximately 15 cM apart on chromosome 8. Thus, the insertion site is within a 15 cM region on the long arm of chromosome 8, near position 117, and in the interval flanked by two markers: Z1B3 and UMC150a Southern Analysis of the Transgenic Event The Bt11 transgenic seeds backcrossed into inbred line HAF031 (deposited with ATCC pursuant to the Budapest Treaty on Apr. 19, 1999 under designation 2044Bt and assigned accession number 203943) were sown in the greenhouse and sprayed with BASTA herbicide at the four leaf stage. Resistant plants and control, untransformed, HAF031 inbred plants were then used for DNA extraction and Southern blot analysis (T. Maniatis, E. F. Fritsch and J. Sambrook, 1982, Molecular Cloning A Laboratory Manual, Cold Spring Harbor Laboratory) The genomic DNA samples were digested with following restriction enzymes and probed with labeled DNA for Btk and PAT gene sequences. The first enzyme combination utilized 2 restriction sites present on the plasmid DNA. The next two enzymes bad only one known location and would be expected to cut the genomic DNA at a distant site in the plant DNA. The actual size of any observed fragment depends on the insertion event. The number of bands can be used to estimate insertion copy number—each gene copy would produce a unique band on the Southern blot.

The results of a Southern blot are summarized in Table 2 These data show that the Bt 11 transgenic lines are derived from a single insertion event containing one gene copy of the Bt and pat gene sequences.

TABLE 2

| Restriction Enzymes | Probe | Predicted | Observed | #Fragment |
|---|---|---|---|---|
| Sal 1 and Sac I | Btk | 1.3 kb | 1.3 kb | 1 |
| Hind III | Btk | >3 kb | ~30 kb | 1 |
| EcoR I | Btk | >5 kb | ~25 kb | 1 |
| PstI and Hind III | PAT | 1.5 kb | 1.5 kb | 1 |
| Hind III | PAT | >2 kb | ~30 kb | 1 |
| EcoR I | PAT | >5 kb | ~25 kb | 1 |

The DNA probe fragments were isolated from the original plasmid vector pZO1502: Btk = Sal I and Sac I fragment and PAT + Sal I fragment.

EXAMPLE 5: Enzymatic Activity of PAT in the Bt Transformed Lines

Fresh tissue samples (3–50 mg) were ground on ice in ~5 volumes of extraction buffer (100 mM Tris-HCL, pH 7.5), 3 mg/ml dithiothreitol and 0.3 mg/ml bovine serum albumin (BAS fraction V). The homogenate was centrifuged to clarity (12,000×g for 5 min). Approximately 2 $\mu$l of extract was added to the reaction mixture containing the extraction buffer plus 125 $\mu$M acetyl CoA and 250 $\mu$M phosphinothricin. The enzymatic reaction was allowed to proceed for 1 hour at 37° C. The reaction mix was then spotted onto TLC silica gel plates (Baker Si250-PA (19C)). The plate was chromatographed for 2–3 hours with isopropanol:NH40H (3:2), air dried and vacuum dried in an oven at 80° C. The plates were then exposed to X-ray film for 1–4 days. The results of a typical assay confirm the presence and enzymatic activity of the PAT protein in the Bt lines.

EXAMPLE 6: Inheritance and Gene Stability

The segregation of the Btk gene and the PAT gene were followed in multiple generations. Eight F1 corn plants identified as containing the Btk and PAT genes were selfed to produce a S1 population. The S1 population was screened for resistance to ECB and Ignite® herbicide. All plants were either resistant to ECB and Ignite or susceptible to both. The segregation ratios were consistent with an expected ratio of 3:1 for a single dominant locus.

EXAMPLE 7: Bt-11 maize versus European Corn Borer Field Trials

Trials were conducted using a randomized complete block design. Two replicates were planted at three locations across three states in two-row plots. Hybrids were grouped according to relative maturity and planted at appropriate sites based on maturity. Southern trials contained six Btk hybrids and four non-Btk control hybrids. The northern trials consisted of eight Btk hybrids and two non-Btk hybrids. Plants were artificially infected as they approached the V6 stage of growth. Approximatety fifty larvae were appplied to ten plants in the first row of each plot every three to four days over a two and one-half week period. By the end of the first generation infesting, each plant had been infected with at least 200 neonate larvae. Just prior to tassel emeregnce, 1–9 leaf damage ratings were assigned to each of the ten plants per plot. The rating scale of Gurthie, W. D., et al. (1960, "Leaf and Sheath Feeding Resistance to the European Corn Borer in Eight Inbred Lines of Dent Corn", Ohio Ag. Exp, Sta. Res. Bull. 860) was used, wherein 1=no damage or few pinholes, 2=small holes on a few leaves, 3=shot-holes on serval leaves, 4=irregular shaped holes on a few leaves, and 9=several leaves with many emerging elongated lesions.

As plants began to shed pollen, second generation ECB infestation began. The first ten plants of the first row of each plot were infected with 40–50 larvae every three to four days over a two and one-half week period. Eventually every plant had been infected with approximately 200 more larvae. After approximately 45 to 50 days, plants were dissected from top to the ground and the total length of tunnels created by ECB feeding was estimated and converted to centimeters for reporting. Analysis of Variance and Least Significant Difference mean separation were used to analyze the results.

Average leaf feeding damage scores were approximately 3.9 on non-Btk hybrids and 1.1 for Btk hybrids wherein 1 on the scale of 1 to 9 represents no damage. Average stalk damage represented as centimeters tunneled per plant, was approximately 4.9 cm in the non-Btk control hybrids. The Btk hybrids displayed only approximately 0.2 cm of tunneling per plant. In all cases, the difference between Btk hybrids and non-Btk hybrids was significant at a P-value of less than 0.01 based on AVOVA and LSD mean separation. Field tests conducted to determined the resistance of Btk hybrids and non-Btk hybrids for Southwestern Corn Borer and Fall Armyworm also indicated that Btk hybrids showed excellent potential for assisting in the control of these insect pests.

EXAMPLE 8: Bt11 Sweet Corn

Inbred backcrossing of Bt 11 event material as described in Example 4 into Novartis (Rogers) elite inbred sweet corn lines was carried out to obtain Bt 11 inbred sweet corn lines, including inbreds R327H ATCC Accession No: 209673, deposited Mar. 11, 1998, R372H ATCC Accession No: 209674, deposited Mar. 11, 1998, R412H ATCC Accession No. 209675, deposited Mar. 11, 1998, R583H ATCC Accession No: 209671, deposited Mar. 11, 1998 and R660H ATCC Accession No: 209672, deposited Mar. 11, 1998 . These inbreds and their F1 hybrid progeny all contain the Btk insert as described above at the location described above and exhibit insect resistance and herbicide resistance as for the other lines descended from the Bt11 event. For example, 2500 seeds of each of these lines were deposited with ATCC prior to the filing of this application pursuant to the Budapest Treaty and accorded accession numbers as follows: R327H: , R372H: , R412H: , R583H: and R660H: . These lines were evaluated at Nampa, Idaho and Stanton, Minn. during the summer and fall of 1997, and characterized in relation to a standard reference inbred (Iowa5125, from North Central Region Plant Introduction Center, Ames, Iowa) having similar background and maturity, as depicted on the following table. (All measurements are in centimeters unless otherwise noted. Colors are according to Munsell color code chart.)

TABLE 3

| Trait | R327H | R372H | R412H | R583H | R660H | Iowa5125 |
|---|---|---|---|---|---|---|
| Kernel color | Yellow-orange | Yellow-orange | Yellow-orange | Yellow-orange | Yellow-orange | Yellow-orange |
| Endosperm type | sul | sul | sul | sh2 | sh2 | sul |
| Maturity (days) | | | | | | |
| emergence to 50% silk | 71 | 70 | 75 | 70 | 77 | 71 |
| emergence to 50% pollen | 68 | 67 | 68 | 66 | 73 | 67 |
| 50% silk to optimal edible quality | 24 | 26 | 25 | 25 | 29 | 25 |
| Plant | | | | | | |
| plant height | 207.0 | 199.7 | 144.0 | 173.8 | 174.8 | 152.8 |
| ear height | 51.8 | 65.9 | 45.3 | 40.1 | 57.0 | 57.5 |
| top ear internode | 17.6 | 15.5 | 10.0 | 15.8 | 13.6 | 13.8 |
| avg. number of tillers | 2.3 | 1.1 | 0.4 | 3.3 | 1.2 | 0.8 |
| avg. number of ears/stalk | 1.8 | 1.9 | 1.7 | 2.1 | 2.0 | 1.3 |
| anthocyanin of brace roots | absent | absent | absent | absent | absent | absent |
| Leaf | | | | | | |
| width of ear node leaf | 7.5 | 6.4 | 8.1 | 7.5 | 9.7 | 7.3 |
| length of ear node leaf | 70.7 | 65.0 | 54.0 | 64.1 | 67.3 | 82.4 |
| no. of leaves above top ear | 6 | 5 | 5 | 5 | 6 | 6 |
| degrees of leaf angle | 49 | 41 | 63 | 46 | 60 | 56 |
| leaf color | very dark green | very dark green | green-yellow | very dark green | green-yellow | green-yellow |

TABLE 3-continued

| Trait | R327H | R372H | R412H | R583H | R660H | Iowa5125 |
|---|---|---|---|---|---|---|
| Tassel | | | | | | |
| no. of primary lateral branches | 15 | 9 | 16 | 10 | 16 | 28 |
| tassel length | 45.8 | 42.0 | 31.0 | 41.6 | 34.5 | 28.4 |
| Ear | | | | | | |
| silk color | green-yellow | green-yellow | green-yellow | green-yellow | light green | light green |
| position at dry husk stage | upright | pendent | horizontal | — | upright | pendent |
| ear length | 14.5 | 16.0 | 15.3 | 16.7 | 15.7 | 13.3 |
| ear diameter at midpoint | 4.1 | 3.8 | 3.74 | 4.67 | 4.05 | 5.33 |
| number of kernel rows | 16 | 16 | 16 | 15 | 16 | 21 |
| cob diameter at midpoint | 2.59 | 2.50 | 2.53 | 2.61 | 2.54 | 2.94 |

EXAMPLE 9: Bt11 Field Corn

Inbred backcrossing of Bt11 event material as described in Example 4 into Novartis (Rogers) elite inbred field corn lines was carried out to obtain Bt 11 inbred field corn lines, for example Yellow Dent inbred lines 2044Bt, 2070Bt, 2100Bt, 2114Bt, 2123Bt, 2227Bt, 2184Bt, 2124Bt, and 2221Bt. These inbreds and their hybrid progeny all contain the Btk insert as described above at the location described above and exhibit insect resistance and herbicide resistance as for the other plants descended from the Bt11 event. 2500 seeds of each of the following lines were deposited with ATCC pursuant to the Budapest Treaty on Apr. 19, 1999 and accorded deposit numbers as follows: 2044Bt: ATCC 203943, 2070Bt: ATCC 203941, 2227Bt: ATCC 203942, 2184Bt: ATCC 203944, and 2221Bt: Bt11 inbreds were also made by marker assisted inbred conversion of the following lines, NP948 (ATCC 209406), NP2017 (ATCC 209543), NP904 (ATCC 209458), NP2010 (ATCC), all deposited with ATCC pursuant to the Budapest Treaty to obtain 2100Bt, 2114Bt, 2123Bt and 2124Bt respectively.

Hybrids from Bt11 inbred conversions were evaluated extensively against hybrids from isogenic, non-transgenic parents in a number of field trials. In general, there was a significant yield advantage to the BT11 version. There was no attempt to control natural infestations of European Corn Borers in these trial locations. Grain moisture at harvest is sometimes slightly higher in the BT11 version. This can often be attributed to the improved plant health, due to reduced stalk rot. In some cases, grain test weight is higher in the BT11 version, which can also reduce the rate of grain dry down. Stalk lodging is typically lower in the BT11 versions. Push test and Late season intactness are also typically better in BT11 versions. In some cases, stay green is better. Plant and ear height are sometimes slightly higher in the BT 11 version. For other traits, no consistent detrimental changes in performance have been observed.

2124Bt, 2221Bt, and 2070Bt are southern (late) maturities, whereas 2044Bt, 2100Bt, 2114Bt, 2227Bt, 2184Bt, and 2123Bt are northern (early) maturities. These inbred Bt lines have the following general characterization:

2044Bt—dark-reddish purple silk, slight pale green color, very slightly faded chlorotic stripes in leaves, medium tall, medium ear-placement, purple tip to glume 2100Bt—green-yellow silk, medium-short plant height, medium low ear placement, green with purple glume, light green overall appearance 2114Bt—dark reddish purple silk, small tassel, slight crook in stalk nodes, slight pale green color, medium tall, medium ear placement, higher yielding than 2044Bt 2227Bt—very thin loose husk at harvest, root lodges, medium plant height, medium ear placement 2184Bt—medium plant height, medium ear placement, very light pollen shedder, green yellow silk color, pale purple anther 2123Bt—green with purple glumes, purple anther, green yellow silk, medium plant height

```
Sequence information
Sequence 1: 35S promoter (EcoR I, Sac I, -35S- Sac I, Kpn I, Sma I)
     1 AATTCGAGCT CGTCAGAAGA CCAGAGGGCT ATTGAGACTT TCAACAAAG GGTAATATCG

61 GGAAACCTCC TCGGATTCCA TTGCCCAGCT ATCTGTCACT TCATCGAAAG GACAGTAGAA

121 AAGGAAGGTG GCTCCTACAA ATGCCATCAT TGCGATAAAG GAAAGGCTAT CGTTCAAGAT

181 GCCTCTACCG ACAGTGGTCC CAAAGATGGA CCCCCACCCA CGAGGAACAT CGTGGAAAAA

241 GAAGACGTTC CAACCACGTC TTCAAAGCAA GTGGATTGAT GTGATATCTC CACTGACGTA

301 AGGGATGACG CACAATCCCA CTATCCTTCG CAAGACCCTT CCTCTATATA AGGAAGTTCA

361 TTTCATTTGG AGAGGACACG CTGAAATCAC CAGTCTCTCT CTACAAATCT ATCTCTCTCT

421 ATTTTCTCCA TAATAATGTG TGAGTAGTTC CCAGATAAGG GAATTAGGGT TCTTATAGGG

481 TTTCGCTCAC GTGTTGAGCA TATAAGAAAC CCTTACGAGC TCGGTACCCG GG
```

-continued

Sequence 2: *Adh1-1S* intron 6 (*BamH* I, -ADH1SIVS6-, *BamH* I, *Xba* I, *Sal* I)

```
   1 GATCCGGAAG GTGCAAGGAT TGCTCGAGCG TCAAGGATCA TTGGTGTCGA CCTGAACCCC
  61 AGCAGATTCG AAGAAGGTAC AGTACACACA CATGTATATA TGTATGATGT ATCCCTTCGA
 121 TCGAAGGCAT GCCTTGGTAT AATCACTGAG TAGTCATTTT ATTACTTTGT TTTGACAAGT
 181 CAGTAGTTCA TCCATTTGTC CCATTTTTTC AGCTTGGAAG TTTGGTTGCA CTGGCACTTG
 241 GTCTAATAAC TGAGTAGTCA TTTTATTACG TTGTTTCGAC AAGTCAGTAG CTCATCCATC
 301 TGTCCCATTT TTTCAGCTAG GAAGTTTGGT TGCACTGGCC TTGGACTAAT AACTGATTAG
 361 TCATTTTATT ACATTGTTTC GACAAGTCAG TAGCTCATCC ATCTGTCCCA TTTTTCAGCT
 421 AGGAAGTTCG GTTGCACTGA ATTTGTGAAC CCAAAAGACC ACAACAAGCC GCGGATCCTC
 481 TAGAGTCGAC
```

Sequence 3: *crylAb* toxic gene region (*Nco* I, -crylAb-, *Bgl* II)

```
   1 CATGGACAAC AACCCAAACA TCAACGAATG CATTCCATAC AACTGCTTGA GTAACCCAGA
  61 AGTTGAAGTA CTTGGTGGAG AACGCATTGA AACCGGTTAC ACTCCCATCG ACATCTCCTT
 121 GTCCTTGACA CAGTTTCTGC TCAGCGAGTT CGTGCCAGGT GCTGGGTTCG TTCTCGGACT
 181 AGTTGACATC ATCTGGGGTA TCTTTGGTCC ATCTCAATGG GATGCATTCC TGGTGCAAAT
 241 TGAGCAGTTG ATCAACCAGA GGATCGAAGA GTTCGCCAGG AACCAGGCCA TCTCTAGGTT
 301 GGAAGGATTG AGCAATCTCT ACCAAATCTA TGCAGAGAGC TTCAGAGAGT GGGAAGCCGA
 361 TCCTACTAAC CCAGCTCTCC GCGAGGAAAT GCGTATTCAA TTCAACGACA TGAACAGCGC
 421 CTTGACCACA GCTATCCCAT TGTTCGCAGT CCAGAACTAC CAAGTTCCTC TCTTGTCCGT
 481 GTACGTTCAA GCAGCTAATC TTCACCTCAG CGTGCTTCGA GACGTTAGCG TGTTTGGGCA
 541 AAGGTGGGGA TTCGATGCTG CAACCATCAA TAGCCGTTAC AACGACCTTA CTAGGCTGAT
 601 TGGAAACTAC ACCGACCACG CTGTTCGTTG GTACAACACT GGCTTGGAGC GTGTCTGGGG
 661 TCCTGATTCT AGAGATTGGA TTAGATACAA CCAGTTCAGG AGAGAATTGA CCCTCACAGT
 721 TTTGGACATT GTGTCTCTCT TCCCGAACTA TGACTCCAGA ACCTACCCTA TCCGTACAGT
 781 GTCCCAACTT ACCAGAGAAA TCTATACTAA CCCAGTTCTT GAGAACTTCG ACGGTAGCTT
 841 CCGTGGTTCT GCCCAAGGTA TCGAAGGCTC CATCAGGAGC CCACACTTGA TGGACATCTT
 901 GAACAGCATA ACTATCTACA CCGATGCTCA CAGAGGAGAG TATTACTGGT CTGGACACCA
 961 GATCATGGCC TCTCCAGTTG GATTCAGCGG GCCCGAGTTT ACCTTTCCTC TCTATGGAAC
1021 TATGGGAAAC GCCGCTCCAC AACAACGTAT CGTTGCTCAA CTAGGTCAGG GTGTCTACAG
1081 AACCTTGTCT TCCACCTTGT ACAGAAGACC CTTCAATATC GGTATCAACA ACCAGCAACT
1141 TTCCGTTCTT GACGGAACAG AGTTCGCCTA TGGAACCTCT TCTAACTTGC CATCCGCTGT
1201 TTACAGAAAG AGCGGAACCG TTGATTCCTT GGACGAAATC CCACCACAGA ACAACAATGT
1261 GCCACCCAGG CAAGGATTCT CCCACAGGTT GAGCCACGTG TCCATGTTCC GTTCCGGATT
1321 CAGCAACAGT TCCGTGAGCA TCATCAGAGC TCCTATGTTC TCATGGATTC ATCGTAGTGC
1381 TGAGTTCAAC AATATCATTC CTTCCTCTCA AATCACCCAA ATCCCATTGA CCAAGTCTAC
1441 TAACCTTGGA TCTGGAACTT CTGTCGTGAA AGGACCAGGC TTCACAGGAG GTGATATTCT
1501 TAGAAGAACT TCTCCTGGCC AGATTAGCAC CCTCAGAGTT AACATCACTG CACCACTTTC
1561 TCAAAGATAT CGTGTCAGGA TTCGTTACGC ATCTACCACA AACTTGCAAT TCCACACCTC
1621 CATCGACGGA AGGCCTATCA ATCAGGGTAA CTTCTCCGCA ACCATGTCAA GCGGCAGCAA
1681 CTTGCAATCC GGCAGCTTCA GAACCGTCGG TTTCACTACT CCTTTCAACT TCTCTAACGG
```

-continued

```
1741 ATCAAGCGTT TCACCCTTA GCGCTCATGT GTTCAATTCT GGCAATGAAG TGTACATTGA

1801 CCGTATTGAG TTTGTGCCTG CCGAAGTTAC CTTCGAGGCT GAGTACTAGC A
```

Sequence 4: NOS terminator (*Bcl* I, -NOS-, *Hind* III)

```
  1 GATCAGGATC GTTCAAACAT TTGGCAATAA AGTTTCTTAA GATTGAATCC TGTTGCCGGT

61 CTTGCGATGA TTATCATATA ATTTCTGTTG AATTACGTTA AGCATGTAAT AATTAACATG

121 TAATGCATGA CGTTATTTAT GAGATGGGTT TTTATGATTA GAGTCCCGCA ATTATACATT

181 TAATACGCGA TAGAAAACAA AATATAGCGC GCAACCTAGG ATAAATTATC GCGCGCGGTG

241 TCATCTATGT TACTAGATCC A
```

Sequence 5: 35S promoter (*BamH* I, -35S-, *Xba* I)

```
  1 GATCCGAACA TGGTGGAGCA CGACACGCTT GTCTACTCCA AAAATATCAA AGATACAGTC

61 TCAGAAGACC AAAGGGCAAT TGAGACTTTT CAACAAAGGG TAATATCCGG AAACCTCCTC

121 GGATTCCATT GCCCAGCTAT CTGTCACTTT ATTGTGAAGA TAGTGGAAAA GGAAGGTGGC

181 TCCTACAAAT GCCATCATTG CGATAAAGGA AAGGCCATCG TTGAAGATGC CTCTGCCGAC

241 AGTGGTCCCA AAGATGGACC CCCACCCACG AGGAGCATCG TGGAAAAAGA AGACGTTCCA

301 ACCACGTCTT CAAAGCAAGT GGATTGATGT GATATCTCCA CTGACGTAAG GGATGACGCA

361 CAATCCCACT ATCCTTCGCA AGACCCTTCC TCTATATAAG GAAGTTCATT TCATTTGGAG

421 AGGACACGCT GAAATCACCA GTCTCTCTCT ACAAATCTAT CTCTCTCTAT AATAATGTGT

481 GAGTAGTTCC CAGATAAGGG AATTAGGGTT CTTATAGGGT TTCGCTCATG TGTTGAGCAT

541 ATAAGAAACC CTTACTCTAG
```

Sequence 6: *Adhl-1S* intron 2 (partial *Asu* II -ADH1SIVS2-, *Xho* I)

```
  1 CGAAGATCCT CTTCACCTCG CTCTGCCACA CCGACGTCTA CTTCTGGGAG GCCAAGGTAT

61 CTAATCAGCC ATCCCATTTG TGATCTTTGT CAGTAGATAT GATCAACAA CTCGCGGTTG

121 ACTTGCGCCT TCTTGGCGGC TTATCTGTCT CAGGGGCAGA CTCCCGTGTT CCCTCGGATC
```

Sequence 7: *Pat* gene (*Sal* I, -Pat-, *Bgl* II *Sal* I, *Pst* I)

```
  1 TCGACATGTC TCCGGAGAGG AGACCAGTTG AGATTAGGCC AGCTACAGCA GCTGATATGG

61 CCGCGGTTTG TGATATCGTT AACCATTACA TTGAGACGTC TACAGTGAAC TTTAGGACAG

121 AGCCACAAAC ACCACAAGAG TGGATTGATG ATCTAGAGAG GTTGCAAGAT AGATACCCTT

181 GGTTGGTTGC TGAGGTTGAG GGTGTTGTGG CTGGTATTGC TTACGCTGGG CCCTGGAAGG

241 CTAGGAACGC TTACGATTGG ACAGTTGAGA GTACTGTTTA CGTGTCACAT AGGCATCAAA

301 GGTTGGGCCT AGGATCCACA TTGTACACAC ATTTGCTTAA GTCTATGGAG GCGCAAGGTT

361 TTAAGTCTGT GGTTGCTGTT ATAGGCCTTC CAAACGATCC ATCTGTTAGG TTGCATGAGG

421 CTTTGGGATA CACAGCCCGG GGTACATTGC GCGCAGCTGG ATACAAGCAT GGTGGATGGC

481 ATGATGTTGG TTTTTGGCAA AGGGATTTTG AGTTGCCAGC TCCTCCAAGG CCAGTTAGGC

541 CAGTTACCCA GATCTGAGTC GACCTGCA
```

Sequence 8: NOS terminator (*Pst* I, -NOS-, *Bgl* II)

```
  1 GATCGTTCAA ACATTTGGCA ATAAAGTTTC TTAAGATTGA ATCCTGTTGC CGGTCTTGCG

61 ATGATTATCA TATAATTTCT GTTGAATTAC GTTAAGCATG TAATAATTAA CATGTAATGC

121 ATGACGTTAT TTATGAGATG GGTTTTTATG ATTAGAGTCC CGCAATTATA CATTTAATAC

181 GCGATAGAAA ACAAAATATA GCGCGCAACC TAGGATAAAT TATCGCGCGC GGTGTCATCT

241 ATGTTACTA
```

-continued

Sequence 9: Complete sequence of pZO1502starting at the *EcoR*I site immediately upstream of the *Bt* gene cassette. The *Bt* gene (nucleotides 1022–2869) and the *pat* gene (nucleotides 4294–4845) are aligned with the amino acid sequence of the respective proteins. The recognition sequences of the *Not*I sites flanking the beta-lactamase (amp) gene are underlined.

```
   1 GAATTCGAGCTCGTCAGAAGACCAGAGGGCTATTGAGACTTTTCAACAAAGGGTAATATCGGGAAACCTCCTCGGATTCC   80

81 ATTGCCCAGCTATCTGTCACTTCATCGAAAGGACAGTAGAAAAGGAAGGTGGCTCCTACAAATGCCATCATTGCGATAAA  160

161 GGAAAGGCTATCGTTCAAGATGCCTCTACCGACAGTGGTCCCAAAGATGGACCCCCACCCACGAGGAACATCGTGGAAAA  240

241 AGAAGACGTTCCAACCACGTCTTCAAAGCAAGTGGATTGATGTGATATCTCCACTGACGTAAGGGATGACGCACAATCCC  320

321 ACTATCCTTCGCAAGACCCTTCCTCTATATAAGGAAGTTCATTTCATTTGGAGAGGACACGCTGAAATCACCAGTCTCTC  400

401 TCTACAAATCTATCTCTCTCTATTTTCTCCATAATAATGTGTGAGTAGTTCCCAGATAAGGGAATTAGGGTTCTTATAGG  480

481 GTTTCGCTCACGTGTTGAGCATATAAGAAACCCCGAGCTCGGTACCCGGGGATCCGGAAGGTGCAAGGATTGCTCGAGCG  560

561 TCAAGGATCATTGGTGTCGACCTGAACCCCAGCAGATTCGAAGAAGGTACAGTACACACACATGTATATATGTATGATGT  640

641 ATCCCTTCGATCGAAGGCATGCCTTGGTATAATCACTGAGTAGTCATTTTATTACTTTGTTTTGACAAGTCAGTAGTTCA  720

721 TCCATTTGTCCCATTTTTTCAGCTTGGAAGTTTGGTTGCACTGGCACTTGGTCTAATAACTGAGTAGTCATTTTATTACG  800

801 TTGTTTCGACAAGTCAGTAGCTCATCCATCTGTCCCATTTTTTCAGCTAGGAAGTTTGGTTGCACTGGCCTTGGACTAAT  880

881 AACTGATTAGTCATTTTATTACATTGTTTCGACAAGTCAGTAGCTCATCCATCTGTCCCATTTTTCAGCTAGGAAGTTCG  960

961 GTTGCACTGAATTTGTGAACCCAAAAGACCACAACAAGCCGCGGATCCTCTAGAGTCGACC ATG GAC AAC AAC   1033
   1                                                               M   D   N   N       4

1034 CCA AAC ATC AAC GAA TGC ATT CCA TAC AAC TGC TTG AGT AAC CCA GAA GTT GAA GTA CTT  1093
   5 P   N   I   N   E   C   I   P   Y   N   C   L   S   N   P   E   V   E   V   L     24

1094 GGT GGA GAA CGC ATT GAA ACC GGT TAC ACT CCC ATC GAC ATC TCC TTG TCC TTG ACA CAG  1153
  25 G   G   E   R   I   E   T   G   Y   T   P   I   D   I   S   L   S   L   T   Q     44

1154 TTT CTG CTC AGC GAG TTC GTG CCA GGT GCT GGG TTC GTT CTC GGA CTA GTT GAC ATC ATC  1213
  45 F   L   L   S   E   F   V   P   G   A   G   F   V   L   G   L   V   D   I   I     64

1214 TGG GGT ATC TTT GGT CCA TCT CAA TGG GAT GCA TTC CTG GTG CAA ATT GAG CAG TTG ATC  1273
  65 W   G   I   F   G   P   S   Q   W   D   A   F   L   V   Q   I   E   Q   L   I     84

1274 AAC CAG AGG ATC GAA GAG TTC GCC AGG AAC CAG GCC ATC TCT AGG TTG GAA GGA TTG AGC  1333
  85 N   Q   R   I   E   E   F   A   R   N   Q   A   I   S   R   L   E   G   L   S    104

1334 AAT CTC TAC CAA ATC TAT GCA GAG AGC TTC AGA GAG TGG GAA GCC GAT CCT ACT AAC CCA  1393
 105 N   L   Y   Q   I   Y   A   E   S   F   R   E   W   E   A   D   P   T   N   P    124

1394 GCT CTC CGC GAG GAA ATG CGT ATT CAA TTC AAC GAC ATG AAC AGC GCC TTG ACC ACA GCT  1453
 125 A   L   R   E   E   M   R   I   Q   F   N   D   M   N   S   A   L   T   T   A    144

1454 ATC CCA TTG TTC GCA GTC CAG AAC TAC CAA GTT CCT CTC TTG TCC GTG TAC GTT CAA GCA  1513
 145 I   P   L   F   A   V   Q   N   Y   Q   V   P   L   L   S   V   Y   V   Q   A    164

1514 GCT AAT CTT CAC CTC AGC GTG CTT CGA GAC GTT AGC GTG TTT GGG CAA AGG TGG GGA TTC  1573
 165 A   N   L   H   L   S   V   L   R   D   V   S   V   F   G   Q   R   W   G   P    184

1574 GAT GCT GCA ACC ATC AAT AGC CGT TAC AAC GAC CTT ACT AGG CTG ATT GGA AAC TAC ACC  1633
 185 D   A   A   T   I   N   S   R   Y   N   D   L   T   R   L   I   G   N   Y   T    204

1634 GAC CAC GCT GTT CGT TGG TAC AAC ACT GGC TTG GAG CGT GTC TGG GGT CCT GAT TCT AGA  1693
 205 D   H   A   V   R   W   Y   N   T   G   L   E   R   V   W   G   P   D   S   R    224

1694 GAT TGG ATT AGA TAC AAC CAG TTC AGG AGA GAA TTG ACC CTC ACA GTT TTG GAC ATT GTG  1753
 225 D   W   I   R   Y   N   Q   F   R   R   E   L   T   L   T   V   L   D   I   V    244

1754 TCT CTC TTC CCG AAC TAT GAC TCC AGA ACC TAC CCT ATC CGT ACA GTG TCC CAA CTT ACC  1813
 245 S   L   F   P   N   Y   D   S   R   T   Y   P   I   R   T   V   S   Q   L   T    264

1814 AGA GAA ATC TAT ACT AAC CCA GTT CTT GAG AAC TTC GAC GGT AGC TTC CGT GGT TCT GCC  1873
 265 R   E   I   Y   T   N   P   V   L   E   N   F   D   G   S   F   R   G   S   A    284

1874 CAA GGT ATC GAA GGC TCC ATC AGG AGC CCA CAC TTG ATG GAC ATC TTG AAC AGC ATA ACT  1933
 265 Q   G   I   E   G   S   I   R   S   P   H   L   M   D   I   L   N   S   I   T    304

1934 ATC TAC ACC GAT GCT CAC AGA GGA GAG TAT TAC TGG TCT GGA CAC CAG ATC ATG GCC TCT  1993
 305 I   Y   T   D   A   H   R   G   E   Y   Y   W   S   G   H   Q   I   M   A   S    324
```

-continued

```
1994 CCA GTT GGA TTC AGC GGG CCC GAG TTT ACC TTT CCT CTC TAT GGA ACT ATG GGA AAC GCC 2053
 325 P   V   G   F   S   G   P   E   F   T   F   P   L   Y   G   T   M   G   N   A    344

2054 GCT CCA CAA CAA CGT ATC GTT GCT CAA CTA GGT CAG GGT GTC TAC AGA ACC TTG TCT TCC 2113
 345 A   P   Q   Q   R   I   V   A   Q   L   G   Q   G   V   Y   R   T   L   S   S    364

2114 ACC TTG TAC AGA AGA CCC TTC AAT ATC GGT ATC AAC AAC CAG CAA CTT TCC GTT CTT GAC 2173
 365 T   L   Y   R   R   P   F   N   I   G   I   N   N   Q   Q   L   S   V   L   D    384

2174 GGA ACA GAG TTC GCC TAT GGA ACC TCT TCT AAC TTG CCA TCC GCT GTT TAC AGA AAG AGC 2233
 385 G   T   E   F   A   Y   G   T   S   S   N   L   P   S   A   V   Y   R   K   S    404

2234 GGA ACC GTT GAT TCC TTG GAC GAA ATC CCA CCA CAG AAC AAC AAT GTG CCA CCC AGG CAA 2293
 405 G   T   V   D   S   L   D   E   I   P   P   Q   N   N   N   V   P   P   R   Q    424

2294 GGA TTC TCC CAC AGG TTG AGC CAC GTG TCC ATG TTC CGT TCC GGA TTC AGC AAC AGT TCC 2353
 425 G   F   S   H   R   L   S   H   V   S   M   F   R   S   G   F   S   N   S   S    444

2354 GTG AGC ATC ATC AGA GCT CCT ATG TTC TCA TGG ATT CAT CGT AGT GCT GAG TTC AAC AAT 2413
 445 V   S   I   I   R   A   P   M   F   S   W   I   H   R   S   A   E   F   N   N    464

2414 ATC ATT CCT TCC TCT CAA ATC ACC CAA ATC CCA TTG ACC AAG TCT ACT AAC CTT GGA TCT 2473
 465 I   I   P   S   S   Q   I   T   Q   I   P   L   T   K   S   T   N   L   G   S    484

2474 GGA ACT TCT GTC GTG AAA GGA CCA GGC TTC ACA GGA GGT GAT ATT CTT AGA AGA ACT TCT 2533
 485 G   T   S   V   V   K   G   P   G   F   T   G   G   D   I   L   R   R   T   S    504

2534 CCT GGC CAG ATT AGC ACC CTC AGA GTT AAC ATC ACT GCA CCA CTT TCT CAA AGA TAT CGT 2593
 505 P   G   Q   I   S   T   L   R   V   N   I   T   A   P   L   S   Q   R   Y   R    524

2594 GTC AGG ATT CGT TAC GCA TCT ACC ACA AAC TTG CAA TTC CAC ACC TCC ATC GAC GGA AGG 2653
 525 V   R   I   R   Y   A   S   T   T   N   L   Q   F   H   T   S   I   D   G   R    544

2654 CCT ATC AAT CAG GGT AAC TTC TCC GCA ACC ATG TCA AGC GGC AGC AAC TTG CAA TCC GGC 2713
 545 P   I   N   Q   G   N   F   S   A   T   M   S   S   G   S   N   L   Q   S   G    564

2714 AGC TTC AGA ACC GTC GGT TTC ACT ACT CCT TTC AAC TTC TCT AAC GGA TCA AGC GTT TTC 2773
 565 S   F   R   T   V   G   F   T   T   P   F   N   F   S   N   G   S   S   V   F    584

2774 ACC CTT AGC GCT CAT GTG TTC AAT TCT GGC AAT GAA GTG TAC ATT GAC CGT ATT GAG TTT 2833
 585 T   L   S   A   H   V   F   N   S   G   N   E   V   Y   I   D   R   I   E   F    604

2834 GTG CCT GCC GAA GTT ACC TTC GAG GCT GAG TAC TAG CAGATCAGGATCGTTCAAACATTTGGCAATAA 2901
 605 V   P   A   E   V   T   F   E   A   E   Y   *                                     616

2902 AGTTTCTTAAGATTGAATCCTGTTGCCGGTCTTGCGATGATTATCATATAATTTCTGTTGAATTACGTTAAGCATGTAAT 2981
2982 AATTAACATGTAATGCATGACGTTATTTATGAGATGGGTTTTTATGATTAGAGTCCCGCAATTATACATTTAATACGCGA 3061
3062 TAGAAAACAAAATATAGCGCGCAACCTAGGATAAATTATCGCGCGCGGTGTCATCTATGTTACTAGATCCAAGCTTGGCA 3141
3142 CTGGCCGTCGTTTTACAACGTCGTGACTGGGAAAACCCTGGCGTTACCCAACTTAATCGCCTTGCAGCACATCCCCCTTT 3221
3222 CGCCAGCTGGCGTAATAGCGAAGAGGCCCGCACCGATCGCCCTTCCCAACAGTTGCGCAGCCTGAATGGCGAATGGCGCC 3301
3302 TGATGCGGTATTTTCTCCTTACGCATCTGTGCGGTATTTCACACCGCATATGGTGCACTCTCAGTACAATCTGCTCTGAT 3381
3382 GCCGCATAGTTAAGCCAGCCCCGACACCCGCCAACACCCGCTGACGCGCCCTGACGGGCTTGTCTGCTCCCGGCATCCGC 3461
3462 TTACAGACAAGCTGTGACCGTCTCCGGGAGCTGCATGTGTCAGAGGTTTTCACCGTCATCACCGAAACGCGCGAGACGAA 3541
3542 AGGGCCAGATCCGAACATGGTGGAGCACGACACGCTTGTCTACTCCAAAAATATCAAAGATACAGTCTCAGAAGACCAAA 3621
3622 GGGCAATTGAGACTTTTCAACAAAGGGTAATATCCGGAAACCTCCTCGGATTCCATTGCCCAGCTATCTGTCACTTTATT 3701
3702 GTGAAGATAGTGGAAAAGGAAGGTGGCTCCTACAAATGCCATCATTGCGATAAAGGAAAGGCCATCGTTGAAGATGCCTC 3781
3782 TGCCGACAGTGGTCCCAAAGATGGACCCCCACCCACGAGGAGCATCGTGGAAAAAGAAGACGTTCCAACCACGTCTTCAA 3861
3862 AGCAAGTGGATTGATGTGATATCTCCACTGACGTAAGGGATGACGCACAATCCCACTATCCTTCGCAAGACCCTTCCTCT 3941
3942 ATATAAGGAAGTTCATTTCATTTGGAGAGGACACGCTGAAATCACCAGTCTCTCTCTACAAATCTATCTCTCTCTATAAT 4021
4022 AATGTGTGAGTAGTTCCCAGATAAGGGAATTAGGGTTCTTATAGGGTTTCGCTCATGTGTTGAGCATATAAGAAACCCTT 4101
4102 ACTCTAGCGAAGATCCTCTTCACCTCGCTCTGCCACACCGACGTCTACTTCTGGGAGGCCAAGGTATCTAATCAGCCATC 4181
4182 CCATTTGTGATCTTTGTCAGTAGATATGATACAACAACTCGCGGTTGACTTGCGCCTTCTTGGCGGCTTATCTGTCTCAG 4261
```

-continued

```
4262 GGGCAGACTCCCGTGTTCCCTCGGATCTCGAC ATG TCT CCG GAG AGG AGA CCA GTT GAG ATT AGG CCA 4329
   1                                  M   S   P   E   R   R   P   V   E   I   R   P   12

4330 GCT ACA GCA GCT GAT ATG GCC GCG GTT TGT GAT ATC GTT AAC CAT TAC ATT GAG ACG TCT 4389
  13  A   T   A   A   D   M   A   A   V   C   D   I   V   N   H   Y   I   E   T   S   32

4390 ACA GTG AAC TTT AGG ACA GAG CCA CAA ACA CCA CAA GAG TGG ATT GAT GAT CTA GAG AGG 4449
  33  T   V   N   F   R   T   E   P   Q   T   P   Q   E   W   I   D   D   L   E   R   52

4450 TTG CAA GAT AGA TAC CCT TGG TTG GTT GCT GAG GTT GAG GGT GTT GTG GCT GGT ATT GCT 4509
  53  L   Q   D   R   Y   P   W   L   V   A   E   V   E   G   V   V   A   G   I   A   72

4510 TAC GCT GGG CCC TGG AAG GCT AGG AAC GCT TAC GAT TGG ACA GTT GAG AGT ACT GTT TAC 4569
  73  Y   A   G   P   W   K   A   R   N   A   Y   D   W   T   V   E   S   T   V   Y   92

4570 GTG TCA CAT AGG CAT CAA AGG TTG GGC CTA GGA TCC ACA TTG TAC ACA CAT TTG CTT AAG 4629
  93  V   S   H   R   H   Q   R   L   G   L   G   S   T   L   Y   T   H   L   L   K   112

4630 TCT ATG GAG GCG CAA GGT TTT AAG TCT GTG GTT GCT GTT ATA GGC CTT CCA AAC GAT CCA 4689
 113  S   M   E   A   Q   G   F   K   S   V   V   A   V   I   G   L   P   N   D   P   132

4690 TCT GTT AGG TTG CAT GAG GCT TTG GGA TAC ACA GCC CGG GGT ACA TTG CGC GCA GCT GGA 4749
 133  S   V   R   L   H   E   A   L   G   Y   T   A   R   G   T   L   R   A   A   G   152

4750 TAC AAG CAT GGT GGA TGG CAT GAT GTT GGT TTT TGG CAA AGG GAT TTT GAG TTG CCA GCT 4809
 153  Y   K   H   G   G   W   H   D   V   G   F   W   Q   R   D   F   E   L   P   A   172

4810 CCT CCA AGG CCA GTT AGG CCA GTT ACC CAG ATC TGA GTCGACCTGCAGATCGTTCAAACATTTGGCAA 4877
 173  P///P///R///P///V///R///P///V///T///Q///I///*                                 184

4878 TAAAGTTTCTTAAGATTGAATCCTGTTGCCGGTCTTGCGATGATTATCATATAATTTCTGTTGAATTACGTTAAGCATGT 4957
4958 AATAATTAACATGTAATGCATGACGTTATTTATGAGATGGGTTTTTATGATTAGAGTCCCGCAATTATACATTTAATACG 5037
5038 CGATAGAAAACAAAATATAGCGCGCAACCTAGGATAAATTATCGCGCGGTGTCATCTATGTTACTAGATCTGGGCCTC 5117
5118 GTGATACGCCTATTTTTATAGGTTAATGTCATGATAATAATGGTTTCTTAGACGTCAGGTGGCACTTTTCGGGGAAATGT 5197
5198 GCGCGGAACCCCTATTTGTTTATTTTTCTAAATACATTCAAATATGTATCCGCTCATGGAGGAGCGGCCGCTCCTCCATG 5277
5278 AGACAATAACCCTGATAAATGCTTCAATAATATTGAAAAGGAAGAGTATGAGTATTCAACATTTCCGTGTCGCCCTTAT 5357
5358 TCCCTTTTTTGCGGCATTTTGCCTTCCTGTTTTTGCTCACCCAGAAACGCTGGTGAAAGTAAAAGATGCTGAAGATCAGT 5437
5438 TGGGTGCACGAGTGGGTTACATCGAACTGGATCTCAACAGCGGTAAGATCCTTGAGAGTTTTCGCCCCGAAGAACGTTTT 5517
5518 CCAATGATGAGCACTTTTAAAGTTCTGCTATGTGGCGCGGTATTATCCCGTATTGACGCCGGGCAAGAGCAACTCGGTCG 5597
5598 CCGCATACACTATTCTCAGAATGACTTGGTTGAGTACTCACCAGTCACAGAAAAGCATCTTACGGATGGCATGACAGTAA 5677
5678 GAGAATTATGCAGTGCTGCCATAACCATGAGTGATAACACTGCGGCCAACTTACTTCTGACAACGATCGGAGGACCGAAG 5757
5758 GAGCTAACCGCTTTTTTGCACAACATGGGGGATCATGTAACTCGCCTTGATCGTTGGGAACCGGAGCTGAATGAAGCCAT 5837
5838 ACCAAACGACGAGCGTGACACCACGATGCCTGTAGCAATGGCAACAACGTTGCGCAAACTATTAACTGGCGAACTACTTA 5917
5918 CTCTAGCTTCCCGGCAACAATTAATAGACTGGATGGAGGCGGATAAAGTTGCAGGACCACTTCTGCGCTCGGCCCTTCCG 5997
5998 GCTGGCTGGTTTATTGCTGATAAATCTGGAGCCGGTGAGCGTGGGTCTCGCGGTATCATTGCAGCACTGGGGCCAGATGG 6077
6078 TAAGCCCTCCCGTATCGTAGTTATCTACACGACGGGGAGTCAGGCAACTATGGATGAACGAAATAGACAGATCGCTGAGA 6157
6158 TAGGTGCCTCACTGATTAAGCATTGGTAACTGTCAGACCAAGTTTACTCATATATACTTTAGATTGATTTAAAACTTCAT 6237
6238 TTTTAATTTAAAAGGATCTAgGTGAAGATCCTTTTTGATAATCTCATGGAGGAGCGGCCGCTCCTCCATGACCAAAATCC 6317
6318 CTTAACGTGAGTTTTCGTTCCACTGAGCGTCAGACCCCGTAGAAAAGATCAAAGGATCTTCTTGAGATCCTTTTTTTCTG 6397
6398 CGCGTAATCTGCTGCTTGCAAACAAAAAAACCACCGCTACCAGCGGTGGTTTGTTTGCCGGATCAAGAGCTACCAACTCT 6477
6478 TTTTCCGAAGGTAACTGGCTTCAGCAGAGCGCAGATACCAAATACTGTCCTTCTAGTGTAGCCGTAGTTAGGCCACCACT 6557
6558 TCAAGAACTCTGTAGCACCGCCTACATACCTCGCTCTGCTAATCCTGTTACCAGTGGCTGCTGCCAGTGGCGATAAGTCG 6637
6638 TGTCTTACCGGGTTGGACTCAAGACGATAGTTACCGGATAAGGCGCAGCGGTCGGGCTGAACGGGGGGTTCGTGCACACA 6717
6718 GCCCAGCTTGGAGCGAACGACCTACACCGAACTGAGATACCTACAGCGTGAGCATTGAGAAAGCGCCACGCTTCCCGAAG 6797
6798 GGAGAAAGGCGGACAGGTATCCGGTAAGCGGCAGGGTCGGAACAGGAGAGCGCACGAGGGAGCTTCCAGGGGGAAACGCC 6877
```

-continued

```
6878 TGGTATCTTTATAGTCCTGTCGGGTTTCGCCACCTCTGACTTGAGCGTCGATTTTTGTGATGCTCGTCAGGGGGCGGAG 6957
6958 CCTATGGAAAAACGCCAGCAACGCGGCCTTTTTACGGTTCCTGGCCTTTTGCTGGCCTTTTGCTCACATGTTCTTTCCTG 7037
7038 CGTTATCCCCTGATTCTGTGGATAACCGTATTACCGCCTTTGAGTGAGCTGATACCGCTCGCCGCAGCCGAACGACCGAG 7117
7118 CGCAGCGAGTCAGTGAGCGAGGAAGCGGAAGAGCGCCCAATACGCAAACCGCCTCTCCCCGCGCGTTGGCCGATTCATTA 7197
7198 ATGCAGCTGGCACGACAGGTTTCCCGACTGGAAAGCGGGCAGTGAGCGCAACGCAATTAATGTGAGTTAGCTCACTCATT 7277
7278 AGGCACCCCAGGCTTTACACTTTATGCTTCCGGCTCGTATGTTGTGTGGAATTGTGAGCGGATAACAATTTCACACAGGA 7357
7358 AACAGCTATGACCATGATTAC                                                           7378
```

It is claimed:

1. Seed of maize inbred line 2044Bt having been deposited under ATCC Accession No. 203943, further comprising a nucleic acid construct with a first expression cassette comprising in operable linkage:
   (i) a CaMV 35S promoter, wherein said promoter is the sequence described in SEQ ID NO: 1;
   (ii) a maize alcohol dehydrogenase intron, wherein said intron is the sequence described in SEQ ID NO: 2;
   (iii) a DNA molecule encoding an insecticidal Cry1Ab protein toxin, wherein said DNA molecule encoding an insecticidal Cry1Ab protein toxin is the sequence described in SEQ ID NO: 3; and
   (iv) a NOS terminator, wherein said terminator is the sequence described in SEQ ID NO: 4.

2. An isolated seed of claim 1.

3. The seed of claim 1, wherein the nucleic acid construct further comprises a second expression cassette comprising in operable linkage:
   (i) a CaMV 35S promoter, wherein said promoter is the sequence described in SEQ ID NO: 5;
   (ii) a maize alcohol dehydrogenase intron, wherein said intron is the sequence described in SEQ ID NO: 6;
   (iii) a DNA molecule encoding a phosphinothricin acetyl transferase, wherein said DNA molecule encoding a phosphinothricin acetyl transferase is the sequence described in SEQ ID NO: 7; and
   (iv) a NOS terminator, wherein said terminator is the sequence described in SEQ ID NO: 8.

4. A maize plant, and parts thereof, of inbred line 2044Bt, seed of said line having been deposited under ATCC Accession No. 203943, said maize plant further comprising a nucleic acid construct with a first expression cassette comprising in operable linkage:
   (i) a CaMV 35S promoter, wherein said promoter is the sequence described in SEQ ID NO: 1;
   (ii) a maize alcohol dehydrogenase intron, wherein said intron is the sequence described in SEQ ID NO: 2;
   (iii) a DNA molecule encoding an insecticidal Cry1Ab protein toxin, wherein said DNA molecule encoding an insecticidal Cry1Ab protein toxin is the sequence described in SEQ ID NO: 3; and
   (iv) a NOS terminator, wherein said terminator is the sequence described in SEQ ID NO: 4.

5. Pollen of the plant of claim 4.

6. An ovule of the plant of claim 4.

7. A maize plant, or parts thereof, having all the genotypic and phenotypic characteristics of a plant of inbred line 2044Bt according to claim 4, seed of said line having been deposited under ATCC Accession No: 203943.

8. A method for producing maize seed comprising crossing a maize plant according to claim 4 with itself or another maize plant according to claim 4.

9. A method for producing hybrid maize seed comprising crossing a maize plant according to claim 4, with a different maize plant to form hybrid maize seed.

10. Hybrid seed produced by the method of claim 9.

11. Hybrid maize plant, or parts thereof, grown from the seed of claim 10.

12. The nucleic acid construct according to claim 4, wherein the nucleic acid construct further comprises a second expression cassette comprising in operable linkage:
   (i) a CaMV 35S promoter, wherein said promoter is the sequence described in SEQ ID NO: 5;
   (ii) a maize alcohol dehydrogenase intron, wherein said intron is the sequence described in SEQ ID NO: 6;
   (iii) a DNA molecule encoding a phosphinothricin acetyl transferase, wherein said DNA molecule encoding a phosphinothricin acetyl transferase is the sequence described in SEQ ID NO: 7; and
   (iv) a NOS terminator, wherein said terminator is the sequence described in SEQ ID NO: 8.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
        (A) LENGTH: 532 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: 35S Promoter (xi) SEQUENCE DESCRIPTION: SEQ ID NO: 1:

```
AATTCGAGCT CGTCAGAAGA CCAGAGGGCT ATTGAGACTT TTCAACAAAG GGTAATATCG    60
GGAAACCTCC TCGGATTCCA TTGCCCAGCT ATCTGTCACT TCATCGAAAG GACAGTAGAA   120
AAGGAAGGTG GCTCCTACAA ATGCCATCAT TGCGATAAAG GAAAGGCTAT CGTTCAAGAT   180
GCCTCTACCG ACAGTGGTCC CAAAGATGGA CCCCCACCCA CGAGGAACAT CGTGGAAAAA   240
GAAGACGTTC CAACCACGTC TTCAAAGCAA GTGGATTGAT GTGATATCTC CACTGACGTA   300
AGGGATGACG CACAATCCCA CTATCCTTCG CAAGACCCTT CCTCTATATA AGGAAGTTCA   360
TTTCATTTGG AGAGGACACG CTGAAATCAC CAGTCTCTCT CTACAAATCT ATCTCTCTCT   420
ATTTTCTCCA TAATAATGTG TGAGTAGTTC CCAGATAAGG GAATTAGGGT TCTTATAGGG   480
TTTCGCTCAC GTGTTGAGCA TATAAGAAAC CCTTACGAGC TCGGTACCCG GG            532
```

(2) INFORMATION FOR SEQ ID NO: 2:

(i) SEQUENCE CHARACTERISTICS:
        (A) LENGTH: 490 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:

(B) CLONE: Adh1-1S intron 6

(xi) SEQUENCE DESCRIPTION: SEQ ID NO: 2:

| | | | | | |
|---|---|---|---|---|---|
| GATCCGGAAG | GTGCAAGGAT | TGCTCGAGCG | TCAAGGATCA | TTGGTGTCGA | CCTGAACCCC | 60 |
| AGCAGATTCG | AAGAAGGTAC | AGTACACACA | CATGTATATA | TGTATGATGT | ATCCCTTCGA | 120 |
| TCGAAGGCAT | GCCTTGGTAT | AATCACTGAG | TAGTCATTTT | ATTACTTTGT | TTTGACAAGT | 180 |
| CAGTAGTTCA | TCCATTTGTC | CCATTTTTTC | AGCTTGGAAG | TTTGGTTGCA | CTGGCACTTG | 240 |
| GTCTAATAAC | TGAGTAGTCA | TTTTATTACG | TTGTTTCGAC | AAGTCAGTAG | CTCATCCATC | 300 |
| TGTCCCATTT | TTTCAGCTAG | GAAGTTTGGT | TGCACTGGCC | TTGGACTAAT | AACTGATTAG | 360 |
| TCATTTTATT | ACATTGTTTC | GACAAGTCAG | TAGCTCATCC | ATCTGTCCCA | TTTTTCAGCT | 420 |
| AGGAAGTTCG | GTTGCACTGA | ATTTGTGAAC | CCAAAAGACC | ACAACAAGCC | GCGGATCCTC | 480 |
| TAGAGTCGAC | | | | | | 490 |

(2) INFORMATION FOR SEQ ID NO: 3:

(i) SEQUENCE CHARACTERISTICS:
        (A) LENGTH: 1851 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: cry1Ab toxic gene region (xi) SEQUENCE DESCRIPTION: SEQ ID NO: 3:

| | | | | | |
|---|---|---|---|---|---|
| CATGGACAAC | AACCCAAACA | TCAACGAATG | CATTCCATAC | AACTGCTTGA | GTAACCCAGA | 60 |
| AGTTGAAGTA | CTTGGTGGAG | AACGCATTGA | AACCGGTTAC | ACTCCCATCG | ACATCTCCTT | 120 |
| GTCCTTGACA | CAGTTTCTGC | TCAGCGAGTT | CGTGCCAGGT | GCTGGGTTCG | TTCTCGGACT | 180 |
| AGTTGACATC | ATCTGGGGTA | TCTTTGGTCC | ATCTCAATGG | GATGCATTCC | TGGTGCAAAT | 240 |
| TGAGCAGTTG | ATCAACCAGA | GGATCGAAGA | GTTCGCCAGG | AACCAGGCCA | TCTCTAGGTT | 300 |
| GGAAGGATTG | AGCAATCTCT | ACCAAATCTA | TGCAGAGAGC | TTCAGAGAGT | GGGAAGCCGA | 360 |
| TCCTACTAAC | CCAGCTCTCC | GCGAGGAAAT | GCGTATTCAA | TTCAACGACA | TGAACAGCGC | 420 |
| CTTGACCACA | GCTATCCCAT | TGTTCGCAGT | CCAGAACTAC | CAAGTTCCTC | TCTTGTCCGT | 480 |
| GTACGTTCAA | GCAGCTAATC | TTCACCTCAG | CGTGCTTCGA | GACGTTAGCG | TGTTTGGGCA | 540 |
| AAGGTGGGGA | TTCGATGCTG | CAACCATCAA | TAGCCGTTAC | AACGACCTTA | CTAGGCTGAT | 600 |
| TGGAAACTAC | ACCGACCACG | CTGTTCGTTG | GTACAACACT | GGCTTGGAGC | GTGTCTGGGG | 660 |
| TCCTGATTCT | AGAGATTGGA | TTAGATACAA | CCAGTTCAGG | AGAGAATTGA | CCCTCACAGT | 720 |
| TTTGGACATT | GTGTCTCTCT | TCCCGAACTA | TGACTCCAGA | ACCTACCCTA | TCCGTACAGT | 780 |
| GTCCCAACTT | ACCAGAGAAA | TCTATACTAA | CCCAGTTCTT | GAGAACTTCG | ACGGTAGCTT | 840 |
| CCGTGGTTCT | GCCCAAGGTA | TCGAAGGCTC | CATCAGGAGC | CCACACTTGA | TGGACATCTT | 900 |
| GAACAGCATA | ACTATCTACA | CCGATGCTCA | CAGAGGAGAG | TATTACTGGT | CTGGACACCA | 960 |
| GATCATGGCC | TCTCCAGTTG | GATTCAGCGG | GCCCGAGTTT | ACCTTTCCTC | TCTATGGAAC | 1020 |
| TATGGGAAAC | GCCGCTCCAC | AACAACGTAT | CGTTGCTCAA | CTAGGTCAGG | GTGTCTACAG | 1080 |
| AACCTTGTCT | TCCACCTTGT | ACAGAAGACC | CTTCAATATC | GGTATCAACA | ACCAGCAACT | 1140 |

| | | |
|---|---|---|
| TTCCGTTCTT GACGGAACAG AGTTCGCCTA TGGAACCTCT TCTAACTTGC CATCCGCTGT | 1200 |
| TTACAGAAAG AGCGGAACCG TTGATTCCTT GGACGAAATC CCACCACAGA ACAACAATGT | 1260 |
| GCCACCCAGG CAAGGATTCT CCCACAGGTT GAGCCACGTG TCCATGTTCC GTTCCGGATT | 1320 |
| CAGCAACAGT TCCGTGAGCA TCATCAGAGC TCCTATGTTC TCATGGATTC ATCGTAGTGC | 1380 |
| TGAGTTCAAC AATATCATTC CTTCCTCTCA AATCACCCAA ATCCCATTGA CCAAGTCTAC | 1440 |
| TAACCTTGGA TCTGGAACTT CTGTCGTGAA AGGACCAGGC TTCACAGGAG GTGATATTCT | 1500 |
| TAGAAGAACT TCTCCTGGCC AGATTAGCAC CCTCAGAGTT AACATCACTG CACCACTTTC | 1560 |
| TCAAAGATAT CGTGTCAGGA TTCGTTACGC ATCTACCACA AACTTGCAAT TCCACACCTC | 1620 |
| CATCGACGGA AGGCCTATCA ATCAGGGTAA CTTCTCCGCA ACCATGTCAA GCGGCAGCAA | 1680 |
| CTTGCAATCC GGCAGCTTCA GAACCGTCGG TTTCACTACT CCTTTCAACT TCTCTAACGG | 1740 |
| ATCAAGCGTT TTCACCCTTA GCGCTCATGT GTTCAATTCG GCAATGAAG TGTACATTGA | 1800 |
| CCGTATTGAG TTTGTGCCTG CCGAAGTTAC CTTCGAGGCT GAGTACTAGC A | 1851 |

(2) INFORMATION FOR SEQ ID NO: 4:

(i) SEQUENCE CHARACTERISTICS:
        (A) LENGTH: 261 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: NOS terminator (xi) SEQUENCE DESCRIPTION: SEQ ID NO: 4:

| | | |
|---|---|---|
| GATCAGGATC GTTCAAACAT TTGGCAATAA AGTTTCTTAA GATTGAATCC TGTTGCCGGT | 60 |
| CTTGCGATGA TTATCATATA ATTTCTGTTG AATTACGTTA AGCATGTAAT AATTAACATG | 120 |
| TAATGCATGA CGTTATTTAT GAGATGGGTT TTTATGATTA GAGTCCCGCA ATTATACATT | 180 |
| TAATACGCGA TAGAAAACAA AATATAGCGC GCAACCTAGG ATAAATTATC GCGCGCGGTG | 240 |
| TCATCTATGT TACTAGATCC A | 261 |

(2) INFORMATION FOR SEQ ID NO: 5:

(i) SEQUENCE CHARACTERISTICS:
        (A) LENGTH: 560 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: 35S Promoter (xi) SEQUENCE DESCRIPTION: SEQ ID NO: 5:

| | | |
|---|---|---|
| GATCCGAACA TGGTGGAGCA CGACACGCTT GTCTACTCCA AAAATATCAA AGATACAGTC | 60 |
| TCAGAAGACC AAAGGGCAAT TGAGACTTTT CAACAAAGGG TAATATCCGG AAACCTCCTC | 120 |

```
GGATTCCATT GCCCAGCTAT CTGTCACTTT ATTGTGAAGA TAGTGGAAAA GGAAGGTGGC      180

TCCTACAAAT GCCATCATTG CGATAAAGGA AAGGCCATCG TTGAAGATGC CTCTGCCGAC      240

AGTGGTCCCA AAGATGGACC CCCACCCACG AGGAGCATCG TGGAAAAAGA AGACGTTCCA      300

ACCACGTCTT CAAAGCAAGT GGATTGATGT GATATCTCCA CTGACGTAAG GGATGACGCA      360

CAATCCCACT ATCCTTCGCA AGACCCTTCC TCTATATAAG GAAGTTCATT TCATTTGGAG      420

AGGACACGCT GAAATCACCA GTCTCTCTCT ACAAATCTAT CTCTCTCTAT AATAATGTGT      480

GAGTAGTTCC CAGATAAGGG AATTAGGGTT CTTATAGGGT TTCGCTCATG TGTTGAGCAT      540

ATAAGAAACC CTTACTCTAG                                                  560

(2) INFORMATION FOR SEQ ID NO: 6:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
         (B) CLONE: Adh1-1S intron 2

(xi) SEQUENCE DESCRIPTION: SEQ ID NO: 6:

CGAAGATCCT CTTCACCTCG CTCTGCCACA CCGACGTCTA CTTCTGGGAG GCCAAGGTAT       60

CTAATCAGCC ATCCCATTTG TGATCTTTGT CAGTAGATAT GATACAACAA CTCGCGGTTG      120

ACTTGCGCCT TCTTGGCGGC TTATCTGTCT CAGGGGCAGA CTCCCGTGTT CCCTCGGATC      180

(2) INFORMATION FOR SEQ ID NO: 7:

(i) SEQUENCE CHARACTERISTICS:
        (A) LENGTH: 568 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
         (B) CLONE: Pat gene (xi) SEQUENCE DESCRIPTION: SEQ ID NO: 7:

TCGACATGTC TCCGGAGAGG AGACCAGTTG AGATTAGGCC AGCTACAGCA GCTGATATGG       60

CCGCGGTTTG TGATATCGTT AACCATTACA TTGAGACGTC TACAGTGAAC TTTAGGACAG      120

AGCCACAAAC ACCACAAGAG TGGATTGATG ATCTAGAGAG GTTGCAAGAT AGATACCCTT      180

GGTTGGTTGC TGAGGTTGAG GGTGTTGTGG CTGGTATTGC TTACGCTGGG CCCTGGAAGG      240

CTAGGAACGC TTACGATTGG ACAGTTGAGA GTACTGTTTA CGTGTCACAT AGGCATCAAA      300

GGTTGGGCCT AGGATCCACA TTGTACACAC ATTTGCTTAA GTCTATGGAG GCGCAAGGTT      360

TTAAGTCTGT GGTTGCTGTT ATAGGCCTTC CAAACGATCC ATCTGTTAGG TTGCATGAGG      420

CTTTGGGATA CACAGCCCGG GGTACATTGC GCGCAGCTGG ATACAAGCAT GGTGGATGGC      480

ATGATGTTGG TTTTTGGCAA AGGGATTTTG AGTTGCCAGC TCCTCCAAGG CCAGTTAGGC      540
```

CAGTTACCCA GATCTGAGTC GACCTGCA                                              568

(2) INFORMATION FOR SEQ ID NO: 8:

(i) SEQUENCE CHARACTERISTICS:
        (A) LENGTH: 249 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: NOS Terminator (xi) SEQUENCE DESCRIPTION: SEQ ID NO: 8:

GATCGTTCAA ACATTTGGCA ATAAAGTTTC TTAAGATTGA ATCCTGTTGC CGGTCTTGCG    60

ATGATTATCA TATAATTTCT GTTGAATTAC GTTAAGCATG TAATAATTAA CATGTAATGC   120

ATGACGTTAT TTATGAGATG GGTTTTTATG ATTAGAGTCC CGCAATTATA CATTTAATAC   180

GCGATAGAAA ACAAAATATA GCGCGCAACC TAGGATAAAT TATCGCGCGC GGTGTCATCT   240

ATGTTACTA                                                          249

(2) INFORMATION FOR SEQ ID NO: 9:

(i) SEQUENCE CHARACTERISTICS:
        (A) LENGTH: 7378 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: Complete sequence of pZO1502

(xi) SEQUENCE DESCRIPTION: SEQ ID NO: 9:

GAATTCGAGC TCGTCAGAAG ACCAGAGGGC TATTGAGACT TTTCAACAAA GGGTAATATC    60

GGGAAACCTC CTCGGATTCC ATTGCCCAGC TATCTGTCAC TTCATCGAAA GGACAGTAGA   120

AAAGGAAGGT GGCTCCTACA AATGCCATCA TTGCGATAAA GGAAAGGCTA TCGTTCAAGA   180

TGCCTCTACC GACAGTGGTC CCAAAGATGG ACCCCCACCC ACGAGGAACA TCGTGGAAAA   240

AGAAGACGTT CCAACCACGT CTTCAAAGCA AGTGGATTGA TGTGATATCT CCACTGACGT   300

AAGGGATGAC GCACAATCCC ACTATCCTTC GCAAGACCCT TCCTCTATAT AAGGAAGTTC   360

ATTTCATTTG GAGAGGACAC GCTGAAATCA CCAGTCTCTC TCTACAAATC TATCTCTCTC   420

TATTTTCTCC ATAATAATGT GTGAGTAGTT CCCAGATAAG GGAATTAGGG TTCTTATAGG   480

GTTTCGCTCA CGTGTTGAGC ATATAAGAAA CCCCGAGCTC GGTACCCGGG GATCCGGAAG   540

GTGCAAGGAT TGCTCGAGCG TCAAGGATCA TTGGTGTCGA CCTGAACCCC AGCAGATTCG   600

AAGAAGGTAC AGTACACACA CATGTATATA TGTATGATGT ATCCCTTCGA TCGAAGGCAT   660

GCCTTGGTAT AATCACTGAG TAGTCATTTT ATTACTTTGT TTTGACAAGT CAGTAGTTCA   720

TCCATTTGTC CCATTTTTTC AGCTTGGAAG TTTGGTTGCA CTGGCACTTG GTCTAATAAC   780

```
TGAGTAGTCA TTTTATTACG TTGTTTCGAC AAGTCAGTAG CTCATCCATC TGTCCCATTT      840

TTTCAGCTAG GAAGTTTGGT TGCACTGGCC TTGGACTAAT AACTGATTAG TCATTTTATT      900

ACATTGTTTC GACAAGTCAG TAGCTCATCC ATCTGTCCCA TTTTTCAGCT AGGAAGTTCG      960

GTTGCACTGA ATTTGTGAAC CCAAAAGACC ACAACAAGCC GCGGATCCTC TAGAGTCGAC     1020

CATGGACAAC AACCCAAACA TCAACGAATG CATTCCATAC AACTGCTTGA GTAACCCAGA     1080

AGTTGAAGTA CTTGGTGGAG AACGCATTGA AACCGGTTAC ACTCCCATCG ACATCTCCTT     1140

GTCCTTGACA CAGTTTCTGC TCAGCGAGTT CGTGCCAGGT GCTGGGTTCG TTCTCGGACT     1200

AGTTGACATC ATCTGGGGTA TCTTTGGTCC ATCTCAATGG GATGCATTCC TGGTGCAAAT     1260

TGAGCAGTTG ATCAACCAGA GGATCGAAGA GTTCGCCAGG AACCAGGCCA TCTCTAGGTT     1320

GGAAGGATTG AGCAATCTCT ACCAAATCTA TGCAGAGAGC TTCAGAGAGT GGGAAGCCGA     1380

TCCTACTAAC CCAGCTCTCC GCGAGGAAAT GCGTATTCAA TTCAACGACA TGAACAGCGC     1440

CTTGACCACA GCTATCCCAT TGTTCGCAGT CCAGAACTAC CAAGTTCCTC TCTTGTCCGT     1500

GTACGTTCAA GCAGCTAATC TTCACCTCAG CGTGCTTCGA GACGTTAGCG TGTTTGGGCA     1560

AAGGTGGGGA TTCGATGCTG CAACCATCAA TAGCCGTTAC AACGACCTTA CTAGGCTGAT     1620

TGGAAACTAC ACCGACCACG CTGTTCGTTG GTACAACACT GGCTTGGAGC GTGTCTGGGG     1680

TCCTGATTCT AGAGATTGGA TTAGATACAA CCAGTTCAGG AGAGAATTGA CCCTCACAGT     1740

TTTGGACATT GTGTCTCTCT TCCCGAACTA TGACTCCAGA ACCTACCCTA TCCGTACAGT     1800

GTCCCAACTT ACCAGAGAAA TCTATACTAA CCCAGTTCTT GAGAACTTCG ACGGTAGCTT     1860

CCGTGGTTCT GCCCAAGGTA TCGAAGGCTC CATCAGGAGC CCACACTTGA TGGACATCTT     1920

GAACAGCATA ACTATCTACA CCGATGCTCA CAGAGGAGAG TATTACTGGT CTGGACACCA     1980

GATCATGGCC TCTCCAGTTG GATTCAGCGG GCCCGAGTTT ACCTTTCCTC TCTATGGAAC     2040

TATGGGAAAC GCCGCTCCAC AACAACGTAT CGTTGCTCAA CTAGGTCAGG GTGTCTACAG     2100

AACCTTGTCT CCACCTTGT ACAGAAGACC CTTCAATATC GGTATCAACA ACCAGCAACT     2160

TTCCGTTCTT GACGGAACAG AGTTCGCCTA TGGAACCTCT TCTAACTTGC CATCCGCTGT     2220

TTACAGAAAG AGCGGAACCG TTGATTCCTT GGACGAAATC CCACCACAGA ACAACAATGT     2280

GCCACCCAGG CAAGGATTCT CCCACAGGTT GAGCCACGTG TCCATGTTCC GTTCGGATT     2340

CAGCAACAGT TCCGTGAGCA TCATCAGAGC TCCTATGTTC TCATGGATTC ATCGTAGTGC     2400

TGAGTTCAAC AATATCATTC CTTCCTCTCA AATCACCCAA ATCCCATTGA CCAAGTCTAC     2460

TAACCTTGGA TCTGGAACTT CTGTCGTGAA AGGACCAGGC TTCACAGGAG GTGATATTCT     2520

TAGAAGAACT TCTCCTGGCC AGATTAGCAC CCTCAGAGTT AACATCACTG CACCACTTTC     2580

TCAAAGATAT CGTGTCAGGA TTCGTTACGC ATCTACCACA AACTTGCAAT TCCACACCTC     2640

CATCGACGGA AGGCCTATCA ATCAGGGTAA CTTCTCCGCA ACCATGTCAA GCGGCAGCAA     2700

CTTGCAATCC GGCAGCTTCA GAACCGTCGG TTTCACTACT CCTTTCAACT TCTCTAACGG     2760

ATCAAGCGTT TTCACCCTTA GCGCTCATGT GTTCAATTCT GGCAATGAAG TGTACATTGA     2820

CCGTATTGAG TTTGTGCCTG CCGAAGTTAC CTTCGAGGCT GAGTACTAGC AGATCAGGAT     2880

CGTTCAAACA TTTGGCAATA AAGTTTCTTA AGATTGAATC CTGTTGCCGG TCTTGCGATG     2940

ATTATCATAT AATTTCTGTT GAATTACGTT AAGCATGTAA TAATTAACAT GTAATGCATG     3000

ACGTTATTTA TGAGATGGGT TTTTATGATT AGAGTCCCGC AATTATACAT TTAATACGCG     3060

ATAGAAAACA AAATATAGCG CGCAACCTAG GATAAATTAT CGCGCGCGGT GTCATCTATG     3120

TTACTAGATC CAAGCTTGGC ACTGGCCGTC GTTTTACAAC GTCGTGACTG GGAAAACCCT     3180
```

```
GGCGTTACCC AACTTAATCG CCTTGCAGCA CATCCCCCTT TCGCCAGCTG GCGTAATAGC    3240

GAAGAGGCCC GCACCGATCG CCCTTCCCAA CAGTTGCGCA GCCTGAATGG CGAATGGCGC    3300

CTGATGCGGT ATTTTCTCCT TACGCATCTG TGCGGTATTT CACACCGCAT ATGGTGCACT    3360

CTCAGTACAA TCTGCTCTGA TGCCGCATAG TTAAGCCAGC CCCGACACCC GCCAACACCC    3420

GCTGACGCGC CCTGACGGGC TTGTCTGCTC CCGGCATCCG CTTACAGACA AGCTGTGACC    3480

GTCTCCGGGA GCTGCATGTG TCAGAGGTTT TCACCGTCAT CACCGAAACG CGCGAGACGA    3540

AAGGGCCAGA TCCGAACATG GTGGAGCACG ACACGCTTGT CTACTCCAAA AATATCAAAG    3600

ATACAGTCTC AGAAGACCAA AGGGCAATTG AGACTTTTCA ACAAAGGGTA ATATCCGGAA    3660

ACCTCCTCGG ATTCCATTGC CCAGCTATCT GTCACTTTAT TGTGAAGATA GTGGAAAAGG    3720

AAGGTGGCTC CTACAAATGC CATCATTGCG ATAAAGGAAA GGCCATCGTT GAAGATGCCT    3780

CTGCCGACAG TGGTCCCAAA GATGGACCCC CACCCACGAG GAGCATCGTG GAAAAAGAAG    3840

ACGTTCCAAC CACGTCTTCA AAGCAAGTGG ATTGATGTGA TATCTCCACT GACGTAAGGG    3900

ATGACGCACA ATCCCACTAT CCTTCGCAAG ACCCTTCCTC TATATAAGGA AGTTCATTTC    3960

ATTTGGAGAG GACACGCTGA AATCACCAGT CTCTCTCTAC AAATCTATCT CTCTCTATAA    4020

TAATGTGTGA GTAGTTCCCA GATAAGGGAA TTAGGGTTCT TATAGGGTTT CGCTCATGTG    4080

TTGAGCATAT AAGAAACCCT TACTCTAGCG AAGATCCTCT TCACCTCGCT CTGCCACACC    4140

GACGTCTACT TCTGGGAGGC CAAGGTATCT AATCAGCCAT CCCATTTGTG ATCTTTGTCA    4200

GTAGATATGA TACAACAACT CGCGGTTGAC TTGCGCCTTC TTGGCGGCTT ATCTGTCTCA    4260

GGGGCAGACT CCCGTGTTCC CTCGGATCTC GACATGTCTC CGGAGAGGAG ACCAGTTGAG    4320

ATTAGGCCAG CTACAGCAGC TGATATGGCC GCGGTTTGTG ATATCGTTAA CCATTACATT    4380

GAGACGTCTA CAGTGAACTT TAGGACAGAG CCACAAACAC CACAAGAGTG GATTGATGAT    4440

CTAGAGAGGT TGCAAGATAG ATACCCTTGG TTGGTTGCTG AGGTTGAGGG TGTTGTGGCT    4500

GGTATTGCTT ACGCTGGGCC CTGGAAGGCT AGGAACGCTT ACGATTGGAC AGTTGAGAGT    4560

ACTGTTTACG TGTCACATAG GCATCAAAGG TTGGGCCTAG GATCCACATT GTACACACAT    4620

TTGCTTAAGT CTATGGAGGC GCAAGGTTTT AAGTCTGTGG TTGCTGTTAT AGGCCTTCCA    4680

AACGATCCAT CTGTTAGGTT GCATGAGGCT TTGGGATACA CAGCCCGGGG TACATTGCGC    4740

GCAGCTGGAT ACAAGCATGG TGGATGGCAT GATGTTGGTT TTTGGCAAAG GGATTTTGAG    4800

TTGCCAGCTC CTCCAAGGCC AGTTAGGCCA GTTACCCAGA TCTGAGTCGA CCTGCAGATC    4860

GTTCAAACAT TTGGCAATAA AGTTTCTTAA GATTGAATCC TGTTGCCGGT CTTGCGATGA    4920

TTATCATATA ATTTCTGTTG AATTACGTTA AGCATGTAAT AATTAACATG TAATGCATGA    4980

CGTTATTTAT GAGATGGGTT TTTATGATTA GAGTCCCGCA ATTATACATT TAATACGCGA    5040

TAGAAAACAA AATATAGCGC GCAACCTAGG ATAAATTATC GCGCGCGGTG TCATCTATGT    5100

TACTAGATCT GGGCCTCGTG ATACGCCTAT TTTTATAGGT TAATGTCATG ATAATAATGG    5160

TTTCTTAGAC GTCAGGTGGC ACTTTTCGGG GAAATGTGCG CGGAACCCCT ATTTGTTTAT    5220

TTTTCTAAAT ACATTCAAAT ATGTATCCGC TCATGAGGA GCGGCCGCTC CTCCATGAGA    5280

CAATAACCCT GATAAATGCT TCAATAATAT TGAAAAAGGA AGAGTATGAG TATTCAACAT    5340

TTCCGTGTCG CCCTTATTCC CTTTTTTGCG GCATTTTGCC TTCCTGTTTT TGCTCACCCA    5400

GAAACGCTGG TGAAAGTAAA AGATGCTGAA GATCAGTTGG GTGCACGAGT GGGTTACATC    5460

GAACTGGATC TCAACAGCGG TAAGATCCTT GAGAGTTTTC GCCCCGAAGA ACGTTTTCCA    5520
```

-continued

```
ATGATGAGCA CTTTTAAAGT TCTGCTATGT GGCGCGGTAT TATCCCGTAT TGACGCCGGG      5580

CAAGAGCAAC TCGGTCGCCG CATACACTAT TCTCAGAATG ACTTGGTTGA GTACTCACCA      5640

GTCACAGAAA AGCATCTTAC GGATGGCATG ACAGTAAGAG AATTATGCAG TGCTGCCATA      5700

ACCATGAGTG ATAACACTGC GGCCAACTTA CTTCTGACAA CGATCGGAGG ACCGAAGGAG      5760

CTAACCGCTT TTTTGCACAA CATGGGGGAT CATGTAACTC GCCTTGATCG TTGGGAACCG      5820

GAGCTGAATG AAGCCATACC AAACGACGAG CGTGACACCA CGATGCCTGT AGCAATGGCA      5880

ACAACGTTGC GCAAACTATT AACTGGCGAA CTACTTACTC TAGCTTCCCG GCAACAATTA      5940

ATAGACTGGA TGGAGGCGGA TAAAGTTGCA GGACCACTTC TGCGCTCGGC CCTTCCGGCT      6000

GGCTGGTTTA TTGCTGATAA ATCTGGAGCC GGTGAGCGTG GGTCTCGCGG TATCATTGCA      6060

GCACTGGGGC CAGATGGTAA GCCCTCCCGT ATCGTAGTTA TCTACACGAC GGGGAGTCAG      6120

GCAACTATGG ATGAACGAAA TAGACAGATC GCTGAGATAG GTGCCTCACT GATTAAGCAT      6180

TGGTAACTGT CAGACCAAGT TTACTCATAT ATACTTTAGA TTGATTTAAA ACTTCATTTT      6240

TAATTTAAAA GGATCTAGGT GAAGATCCTT TTTGATAATC TCATGGAGGA GCGGCCGCTC      6300

CTCCATGACC AAAATCCCTT AACGTGAGTT TTCGTTCCAC TGAGCGTCAG ACCCCGTAGA      6360

AAAGATCAAA GGATCTTCTT GAGATCCTTT TTTTCTGCGC GTAATCTGCT GCTTGCAAAC      6420

AAAAAAACCA CCGCTACCAG CGGTGGTTTG TTTGCCGGAT CAAGAGCTAC CAACTCTTTT      6480

TCCGAAGGTA ACTGGCTTCA GCAGAGCGCA GATACCAAAT ACTGTCCTTC TAGTGTAGCC      6540

GTAGTTAGGC CACCACTTCA AGAACTCTGT AGCACCGCCT ACATACCTCG CTCTGCTAAT      6600

CCTGTTACCA GTGGCTGCTG CCAGTGGCGA TAAGTCGTGT CTTACCGGGT TGGACTCAAG      6660

ACGATAGTTA CCGGATAAGG CGCAGCGGTC GGGCTGAACG GGGGGTTCGT GCACACAGCC      6720

CAGCTTGGAG CGAACGACCT ACACCGAACT GAGATACCTA CAGCGTGAGC ATTGAGAAAG      6780

CGCCACGCTT CCCGAAGGGA GAAAGGCGGA CAGGTATCCG GTAAGCGGCA GGGTCGGAAC      6840

AGGAGAGCGC ACGAGGGAGC TTCCAGGGGG AAACGCCTGG TATCTTTATA GTCCTGTCGG      6900

GTTTCGCCAC CTCTGACTTG AGCGTCGATT TTTGTGATGC TCGTCAGGGG GGCGGAGCCT      6960

ATGGAAAAAC GCCAGCAACG CGGCCTTTTT ACGGTTCCTG GCCTTTTGCT GGCCTTTTGC      7020

TCACATGTTC TTTCCTGCGT TATCCCCTGA TTCTGTGGAT AACCGTATTA CCGCCTTTGA      7080

GTGAGCTGAT ACCGCTCGCC GCAGCCGAAC GACCGAGCGC AGCGAGTCAG TGAGCGAGGA      7140

AGCGGAAGAG CGCCCAATAC GCAAACCGCC TCTCCCCGCG CGTTGGCCGA TTCATTAATG      7200

CAGCTGGCAC GACAGGTTTC CCGACTGGAA AGCGGGCAGT GAGCGCAACG CAATTAATGT      7260

GAGTTAGCTC ACTCATTAGG CACCCCAGGC TTTACACTTT ATGCTTCCGG CTCGTATGTT      7320

GTGTGGAATT GTGAGCGGAT AACAATTTCA CACAGGAAAC AGCTATGACC ATGATTAC       7378
```

(2) INFORMATION FOR SEQ ID NO: 10:

(i) SEQUENCE CHARACTERISTICS:
        (A) LENGTH: 615 amino acids
        (B) TYPE: amino acid
        (C) STRANDEDNESS: unknown
        (D) TOPOLOGY: linear (ii) MOLECULE TYPE: protein (iii) HYPOTHETICAL: NO (iii) ANTI-SENSE: NO (vi) ORIGINAL SOURCE:
        (A) ORGANISM: Bacillus thuringiensis -continued (vii) IMMEDIATE SOURCE:
(B) CLONE: Bt protein (xi) SEQUENCE DESCRIPTION: SEQ ID NO: 10:

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
```

-continued

```
                385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Val Ser Ile Ile
                435                 440                 445

Arg Ala Pro Met Phe Ser Trp Ile His Arg Ser Ala Glu Phe Asn Asn
                450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
                500                 505                 510

Val Asn Ile Thr Ala Pro Leu Ser Gln Arg Tyr Arg Val Arg Ile Arg
                515                 520                 525

Tyr Ala Ser Thr Thr Asn Leu Gln Phe His Thr Ser Ile Asp Gly Arg
                530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
                580                 585                 590

Ser Gly Asn Glu Val Tyr Ile Asp Arg Ile Glu Phe Val Pro Ala Glu
                595                 600                 605

Val Thr Phe Glu Ala Glu Tyr
                610                 615

(2) INFORMATION FOR SEQ ID NO: 11:

(i) SEQUENCE CHARACTERISTICS:
         (A) LENGTH: 183 amino acids
         (B) TYPE: amino acid
         (C) STRANDEDNESS: unknown
         (D) TOPOLOGY: linear (ii) MOLECULE TYPE: protein (iii) HYPOTHETICAL: NO (iii) ANTI-SENSE: NO (vii) IMMEDIATE SOURCE:
         (B) CLONE: Pat protein (xi) SEQUENCE DESCRIPTION: SEQ ID NO: 11:

Met Ser Pro Glu Arg Arg Pro Val Glu Ile Arg Pro Ala Thr Ala Ala
1               5                   10                  15

Asp Met Ala Ala Val Cys Asp Ile Val Asn His Tyr Ile Glu Thr Ser
                20                  25                  30

Thr Val Asn Phe Arg Thr Glu Pro Gln Thr Pro Gln Glu Trp Ile Asp
            35                  40                  45

Asp Leu Glu Arg Leu Gln Asp Arg Tyr Pro Trp Leu Val Ala Glu Val
        50                  55                  60

Glu Gly Val Val Ala Gly Ile Ala Tyr Ala Gly Pro Trp Lys Ala Arg
65                  70                  75                  80
```

-continued

```
Asn Ala Tyr Asp Trp Thr Val Glu Ser Thr Val Tyr Val Ser His Arg
             85                  90                  95

His Gln Arg Leu Gly Leu Gly Ser Thr Leu Tyr Thr His Leu Leu Lys
            100                 105                 110

Ser Met Glu Ala Gln Gly Phe Lys Ser Val Val Ala Val Ile Gly Leu
            115             120                 125

Pro Asn Asp Pro Ser Val Arg Leu His Glu Ala Leu Gly Tyr Thr Ala
        130                 135                 140

Arg Gly Thr Leu Arg Ala Ala Gly Tyr Lys His Gly Gly Trp His Asp
145             150                 155                 160

Val Gly Phe Trp Gln Arg Asp Phe Glu Leu Pro Ala Pro Pro Arg Pro
                165                 170                 175

Val Arg Pro Val Thr Gln Ile
                180
```